United States Patent [19]

Wu et al.

[11] Patent Number: 5,186,865
[45] Date of Patent: Feb. 16, 1993

[54] ELECTRO-OPTICAL MATERIALS AND LIGHT MODULATOR DEVICES CONTAINING SAME

[75] Inventors: Chengjiu Wu, Morristown; Ajay Nahata, Madison; Michael J. McFarland, Washington; Keith Horn, Long Valley; James T. Yardley, Morristown, all of N.J.

[73] Assignee: Allied-Signal Inc., Morris Township, Morris County, N.J.

[21] Appl. No.: 770,373

[22] Filed: Oct. 3, 1991

Related U.S. Application Data

[62] Division of Ser. No. 456,420, Dec. 26, 1989, Pat. No. 5,061,404.

[51] Int. Cl.$^5$ .................. F21V 9/00; C09B 29/039; C09B 29/09; C09B 29/36; C07D 277/04
[52] U.S. Cl. .................. 252/582; 548/146; 548/148; 548/162; 548/191; 534/653; 534/753; 534/795
[58] Field of Search .................. 252/299.01, 582, 587; 548/146, 148, 153, 162, 191; 534/653, 659, 665, 752, 753, 778, 795

[56] References Cited

U.S. PATENT DOCUMENTS 4,565,424  1/1986  Huffman et al. ............... 252/299.01
4,752,820  6/1988  Kuroiwa et al. .................. 365/108

FOREIGN PATENT DOCUMENTS 58-02351  1/1983  Japan .
1508500   4/1978  United Kingdom .
2204053  11/1988  United Kingdom .

*Primary Examiner*—Robert L. Stoll
*Assistant Examiner*—Shean C. Wu
*Attorney, Agent, or Firm*—Gerhard H. Fuchs; Richard C. Stewart

[57] ABSTRACT

Azo-type optically active compounds and polymers are provided based on compounds of the general structure

[substituted aryl]—N=N—[substituted aryl]

wherein aryl substituents are introduced which hinder or prohibit rotation around the single bonds of the —N=N— central moiety (as well as around certain other single bonds), to provide "planarized" structures having improved optically active properties, especially electro-optically active properties. These compounds and polymers find use in optically active waveguides.

5 Claims, No Drawings

ELECTRO-OPTICAL MATERIALS AND LIGHT MODULATOR DEVICES CONTAINING SAME

This application is a division of application Ser. No. 456,420, filed Dec. 26, 1989, now U.S. Pat. No. 5,061,404.

FIELD OF THE INVENTION

This invention relates to the field of organic electro-optically active compounds and polymers, and provides such compounds and polymers, as well as monomeric compositions for forming such polymers. The invention further provides electro-optical light modulator devices containing such compounds and polymers.

BACKGROUND OF THE INVENTION

There is growing interest in materials which have high electro-optical (EO) and nonlinear optical (NLO) responses. These optically active materials have conventionally been of inorganic nature, such as $LiNbO_3$, in which the EO response, caused by atomic motions in the crystalline lattice, is slow compared to optical frequencies. Of more recent development are organic polymeric EO materials. In these, the rapid moving $\pi$-electrons in a conjugated framework are responsible for the EO properties. The advantages of using EO polymeric materials lie in their superior EO properties (large EO response over a wide frequency range, fast response time, low dielectric constant, higher laser damage threshold, etc.), better processing characteristics, compatibility with a variety of substrates, and the opportunity to manipulate organic molecular structures to optimize the above properties.

Electro-optically responsive polymeric media have been developed in which a particular molecular entity or functionality, denoted here by the term "molecular electro-optical transducer", is chemically incorporated into an amorphous polymer. The polymer may be fabricated into a suitable form (typically a thin film formed by spin-casting). If such material is "poled", that is to say it is heated to a temperature near or above its glass transition temperature, $T_g$, and is subjected to an applied electric field of appropriate magnitude for a suitable period of time, and is thereafter cooled to temperatures considerably below the $T_g$, a non-centrosymmetric orientation is imparted to the molecular transducer and the material acquires an electro-optic response, that is, the index of refraction of the material will change in direct linear response to an applied electric field. According to a theory [K. D. Singer et al., Appl. Phys. Lett. 49, (1986), 248] which has been said to apply to this situation, the major electro-optic coefficient is determined by the following factors:

(1) number density of molecular transducers, N/V (molecules/cm$^3$);
(2) molecular hyperpolarizability of the transducer, $\beta_{EO}$ (esu);
(3) permanent dipole moment of the transducer, $\mu$ (esu or debye);
(4) applied electric field during "poling", $E_p$ (statvolt/cm);
(5) glass transition temperature, $T_g$ (°K.);
(6) indices of refraction of the medium, n;
(7) "local field factors, f, which for polymer systems are generally approximately unity.

According to this theory, the observed electro-optic coefficient should be given by:

$$r \approx (N/V)(\mu E_p / 5kT_g)\beta_{EO}$$

Thus r is optimized by maximizing (N/V), $\mu$, $E_p$, and importantly $\beta_{EO}$ and by minimizing $T_g$ (subject to restriction that $T_g >$ temperatures of use).

The exact nature of the molecular characteristics which determine $\beta_{EO}$ has not been fully elucidated. However, on the basis of a simple theory it is said that transducers with large $\beta$ are characterized by a large permanent dipole change upon electronic excitation, by a strong oscillator strength for the lowest energy electronic absorption, and by relative closeness of the lowest energy absorption wavelength to the incident wavelength (limited however by the loss of incident radiation by absorption if the absorption wavelength is too close to the incident wavelength).

For electro-optic processes, the molecular transducer must have a dipole with delocalized electron density. Typically, the dipole is constructed by attaching electron-donating (EDG) and electron-withdrawing (EWG) substituents at either end of a conjugated ($\pi$) framework. The NLO activity of the transducer as measured from $\beta$ is determined by the choice of the EDG and EWG, and the length of the $\pi$-system. Higher activity is achieved with stronger donor and acceptor and longer $\pi$-chain. Typical electron-donating substituents are $-NH_2$, $NHR$, $-NR_2$, $-SR$, $-OR$, etc. Typical electron-withdrawing substituents include $-CN$, $-NO_2$, $-CO_2R$, $-C(CN)=C(CN)_2$, etc. Typical $\pi$-units are alkynyl ($-C\equiv C-$), alkenyl and heteroalkenyl (such as $-CH=CH-$, $-N=N-$, $-CH=N-$); aryl and heteroaryl (such as phenyl, biphenyl, pyridinyl) and their various combinations (such as aryl-$CH=CH$-aryl, aryl-$N=N$-aryl, aryl-$CH=N$-aryl).

The prior art describes a number of molecular transducing groups useful for creating electro-optic polymers. The prior art also teaches that the transducer may be attached through a chemical "handle" directly to a pre-existing polymer or to a suitable polymer precursor (monomer) which could later be converted into a polymer. The transducers of the prior art include structures of the type EWG-phenyl-azo-phenyl-$NR_2$ wherein EWG denotes an electron withdrawing group. We have found that by making certain modifications to the azo-based transducers, new transducers having enhanced electro-optical properties are obtained. These new transducers, compositions and polymers based thereon, monomeric compositions for making such polymers, and utilization thereof in light modulator devices, especially electro-optical light modulator devices, are the objects of the present invention, as to be described in detail below.

SUMMARY OF THE INVENTION

First, the present invention provides compounds of the formula:

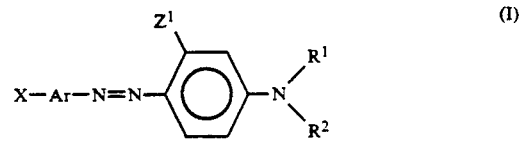
(I)

wherein
(a) X is selected from the group consisting of:
(1) $-NO_2$, (2) —CN,
(3) —COOR³ wherein R³ is alkyl, straight chain, cyclic or branched having 1-20 carbon atoms,
(4) —CH=C(CN)₂ and
(5) —C(CN)=C(CN)₂;
(b) Ar is selected from the group consisting of

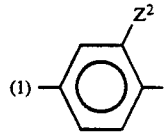

wherein Z² is
(i) —H
(ii) —OH
(iii) —OC—(O)—CH=CH₂
(iv) —OC—(O)—C(CH₃)=CH₂

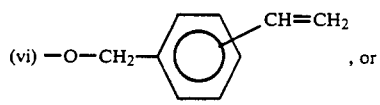, or (vii) —O(CH₂)₂—OCH=CH₂;

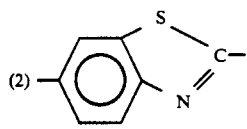

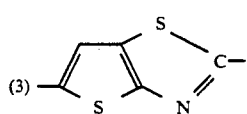

(c) Z¹ is selected from the group consisting of —H and —OH;
(d) R¹ is selected from the group consisting of
(1) —H,
(2) alkyl, straight chain, branched or cyclic, having about 1-20 carbon atoms,
(3) —C$_n$H$_{2n}$OH, wherein n is an integer of from about 1-20,
(4) —(CH₂)$_m$—CH=CH₂, wherein m is an integer of from about 1-20,

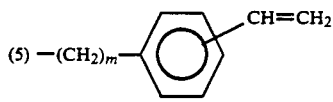

wherein m is an integer of from about 1-20 and the —CH=CH₂ substituent is in the m- or p- position,
(6) —(CH₂)$_m$—O—M wherein m is an integer of from about 1-10, and wherein M is
(i) —CH=CH₂,
(ii) —C(O)—CH=CH₂,
(iii) —C(O)—C(CH₃)=CH₂,

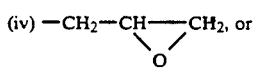

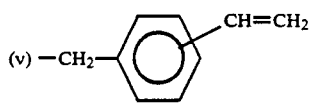

wherein the —CH=CH₂ substituent is in the m- or p- position and
(7) an alkylene bridging group having 2 to 4 carbon atoms connecting the N atom to the o- position of the aromatic ring to which the N atom is attached; and
(e) R² is selected from the group consisting of
(1) —H,
(2) alkyl, straight chain, branched or cyclic, having about 1-20 carbon atoms,
(3) —C$_n$H$_{2n}$OH wherein n is an integer of from about 1-20, and
(4) an alkylene bridging group having 2 to 4 carbon atoms connecting the N atom to the o- position of the aromatic ring to which the N atom is attached;
with the proviso that Z¹ and Z² may not both be H if neither one nor both of R¹ and R² represent an alkylene bridging group having 2 to 4 carbon atoms connecting the N atom to the o- position of the aromatic ring to which the N atom is attached.

Second, the present invention provides optically active (optically non-linear or electro-optically active), especially electro-optically active polymer compositions comprising a compound of formula (I), above, together with an optically clear polymer, generally an amorphous polymer, suitably selected from the group consisting of polymethylmethacrylate (PMMA), polystyrene and polycarbonate, wherein said compound of formula (I) comprises of from about 1 to about 50 percent by weight of the combined weight of the compound and the polymer. These compositions can be applied to suitable substrates, from the melt or from solution in a suitable solvent, to form a film which, after poling as above described, is an effective component in light modulator devices.

Third, the present invention provides optically active, especially electro-optically active vinyl monomeric compositions, including acrylic compositions which can be polymerized using generally known polymerization procedures to form optically active, especially electro-optically active homopolymers, or which can be copolymerized with other monomers of the type capable of forming optically clear, generally amorphous polymers, such as methyl or higher alkyl methacrylate, methyl or higher alkyl acrylate, acrylamide, methacrylamide, styrene or substituted styrene. These homopolymers and copolymers are suitable for fabrication into effective light modulator devices. The monomeric compositions of the present invention are those of general formula (I), above, wherein R¹ is selected from the group consisting of (a) —(CH₂)$_m$—CH=CH₂ wherein m is an integer of from about 1-20, (b)

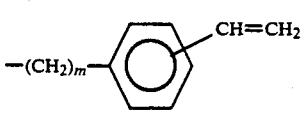

wherein m is an integer of from about 1 to 20, and the —CH=CH₂ substituent is in the m- or p- position, and (c) —CH₂)$_m$—O—M wherein M is selected from the group consisting of —CH=CH₂, —C(O)—CH=CH₂, C(O)—C(CH₃)=CH₂, or

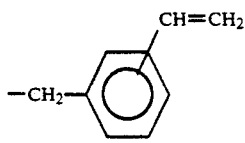

wherein the —CH=CH₂ substituent is in the m- or p-position.

Fourth, the present invention provide linear homopolymers of the vinyl monomeric compositions described under third, above. These polymers are obtained using known polymerization procedures; they can be used as active components of light modulator devices, generally but not necessarily of the electro-optical type. These polymers are characterized by having pendent groups of the transducer moieties bound to a backbone chain, built up of recurring units as illustrated below:

third, above, with comonomers selected from the group consisting of methyl or higher alkyl methacrylate, methyl or higher alkyl acrylate, acrylamide, methacrylamide, styrene or substituted styrene. These copolymers are obtained using known polymerization procedures; they also can be used as active components of light modulator devices, generally but not necessarily of the electro-optical type. These copolymers are also characterized by having pendant groups of the transducer moieties bound to a backbone chain.

Sixth, the present invention provides light modulator devices comprising as an active component a member selected from the group consisting of a compound of formula (I), above; a polymer composition comprising a compound of formula (I), above, together with an optically clear polymer; a linear polymer of any of formulas (II) through (VII), above, or of a copolymer of a vinyl monomeric composition described under third, above, with a comonomer selected from the group consisting of methyl or higher alkyl methacrylate, methyl or higher alkyl acrylate, acrylamide, methacrylamide, styrene or substituted styrene. The light modulator devices

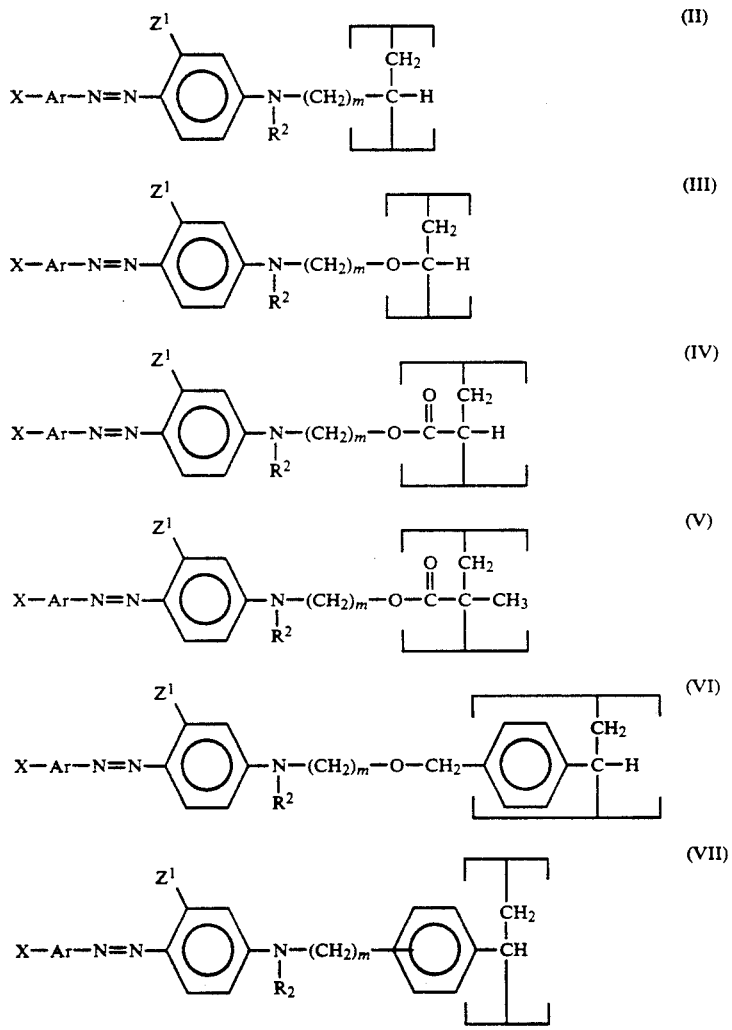

In formulas (II) through (VII), above, X, Ar, $Z^1$, $R^2$ and m have the same meanings as described, above, in connection formula (I).

Fifth, the present invention provides copolymers of the vinyl monomeric compositions described under may be non-linear optic devices or, as is preferred, electro-optical devices. Suitably, they can be in the form of electro-optically active waveguides.

DETAILED DESCRIPTION OF THE INVENTION, OF THE PREFERRED EMBODIMENTS, AND OF THE BEST MODE PRESENTLY CONTEMPLATED FOR ITS PRACTICE

Azo-type electro-optic transducers based on EWG-phenyl-azo-phenyl-NR$_2$ structure in which EWG denotes certain electron withdrawing groups are well known [see, e.g., Marks et al., Macromolecules, 20, 2324 (1987); Hill et al. in R. A. Hann and D. Bloor, Ed., "Organic Materials for Nonlinear Optics", Royal Soc. Chem., 1989, 404; Singer et al., Appl. Phys. Lett. 53, 1800 (1988); European Patent 0.235,506]. These are generally of the structure:

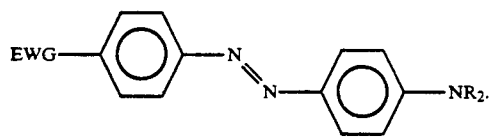

These structures provide for rotation about the indicated axes. Upon exposure to actinic radiation, these structures are also known to exhibit cis-trans isomerization which alters the optical properties of media containing these structures, giving rise to undesirable absorptions and destroying optical activity.

Azo compounds generally exist in cis- and trans forms:

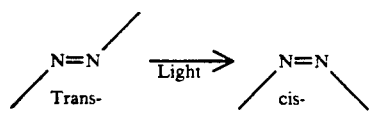

As a rule, the trans- form is more stable. However, if a trans- molecule absorbs light, it can undergo isomerization to the cis- form (although often with low probability in the solid state). Typically, the cis- form absorbs light can create highly absorbing species. It is a feature of this invention that planarization (as described in more detail below) of the aromatic groups with the azo groups significantly decreases the probability of cis-trans-isomerization particularly where two planarizing groups ($Z^1+Z^2$) are present. We have found that by making certain substitutions on the above noted prior art structures, their optical activity (NLO and EO), especially their electro-optical performance can be greatly enhanced, and their resistance to adverse photochemical transformation can be improved. We hypothesize that the substitutions contemplated by us tend to inhibit rotation about one, or more, or all of the indicated axes, thereby "planarizing" the structure, and that a planar structure is important for providing effective communication between the EWG and the electron donating groups NR$_2$. In prior art compounds, we believe the propensity for planarization is limited because the sigma single bonds remain free to rotate. Our invention provides means for prohibiting, or at least inhibiting, rotation about any one of the indicated single bonds in the above structure.

To prohibit the rotation of phenyl-NR$_2$ bond and also to confine the lone pair electrons of the nitrogen to parallel the phenyl $\pi$-orbital, we provide structure such as indoline, indole, 1,2,3,4-tetrahydroquinoline, or julolidine in which the nitrogen atom is further connected to the ortho position of the phenyl ring by a short alkylene bridging group. Such structures include:

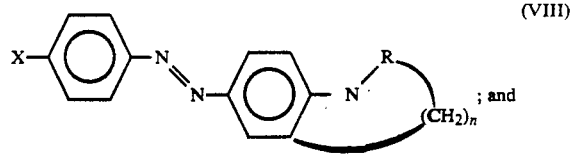

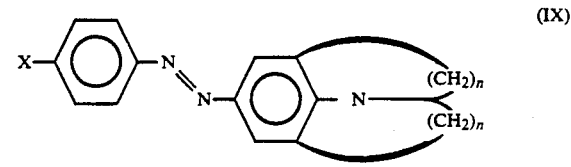

wherein X has the meaning given above in connection with formula (I) and n is an integer of from 2 to 4.

To inhibit the rotation of the phenyl-azo bond and also to improve the stability of the trans-isomer towards photoisomerization to cis-isomer, we use structure which contain hydrogen bond promoting substituents at the ortho position of the azo, such as:

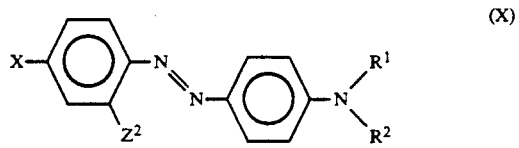

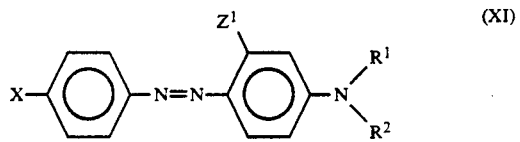

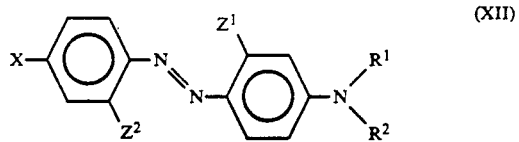

wherein X; $Z^1$; $Z^2$; $R^1$ and $R^2$ all have the meaning given above in connection with formula (I).

The above approaches for planarization may be combined to obtain structures of the type:

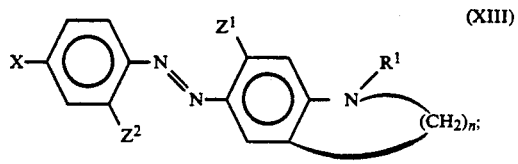

and

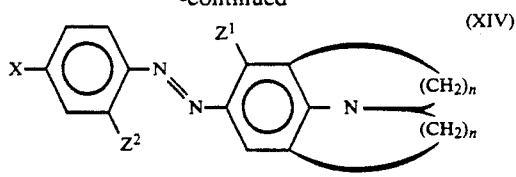

(XIV)

In addition, this invention provides novel transducers in which the conjunction length has been increased by inclusion of a thiazole group and in which planarization is provided:

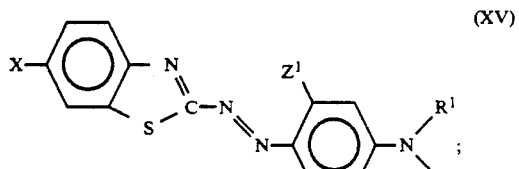

(XV)

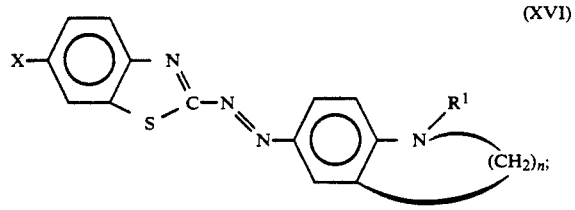

(XVI)

and

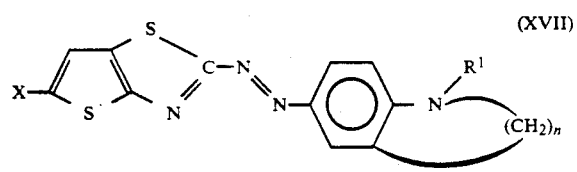

(XVII)

wherein X, $Z^1$, $R^1$ and $R^2$ all have the meaning given above in connection with formula (I) and n is an integer of from about 2 to 4. Transducers incorporating the thiazole group constitute a preferred class, because of their generally enhanced electro-optical properties resulting from the increase in conjugation length.

With reference to the above formulas (I) through (XVII), (XIX) and (XX) the alkylene bridging group ($R^2$) preferably has 2 or 3 carbon atoms, more preferably 2 carbon atoms. The reason for this is that 2 or 3 carbon atoms in this structure form a 5-or 6-member ring known to provide for rigid stable chemical structures. For the 5-member ring (2 carbon atoms) standard models show that the preferred geometry provides for a p-orbital on the N to be maintained parallel to the π-aromatic electron system. This will enhance the conjugation (the electronic interaction) between the electron withdrawing group and the electron donating group.

The $Z^1$ and $Z^2$ groups are those which exhibit the-strong hydrogen bonding character toward —N=N— groups; most preferably, $Z^1$ and/or $Z^2$ are OH.

Where hydrogen bonds are used for planarization, the locations of $Z^1$ and $Z^2$ are equally preferable, although use of OH at the $Z^1$ position potentially could allow the existence of tautomeric forms such as

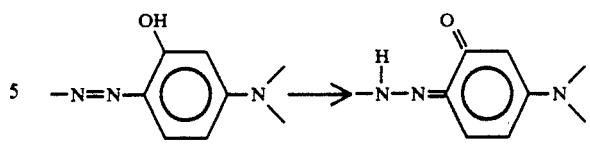

which may introduce deleterious effects such as strong absorption at the operating wavelength.

In general, polymeric forms of the invention are preferred to those involving dissolution of monomeric species within a polymer matrix. This is because:

(a) monomeric materials tend to evaporate or "bake out" during the baking processes normally employed to remove solvent;

(b) monomeric materials tend to aggregate or phase separate—especially at concentrations about 10% by weight;

(c) solid solutions at high concentrations of solute generally have poorer physical properties and poorer physical integrity;

(d) solid solutions potentially have greater health and safety hazard to those working with them as some of these monomeric materials might be expected to be carcinogens;

(e) poled films of solid solutions are reported to "relax" to less ordered states more rapidly than polymeric versions.

In general, the greatest electro-optic response is obtained for polymers containing the greatest concentration of transducer. Thus homopolymers of this invention are preferred. However, homopolymers may sometimes present difficulties in processability such a failure to form high quality thin film. Copolymers with methyl methacrylate perform well with 5-95 mole percent of the monomers of this invention. Copolymerization with different monomers provides a means for ranging/controlling the glass transition temperature $T_g$ of the copolymer.

Preparation of the compositions of formula (I), above, all of which are characterized by the presence of a diazo group, —N=N—, utilizes generally applicable, known azo dye chemistry. In the first step, a primary amine starting material of the formula:

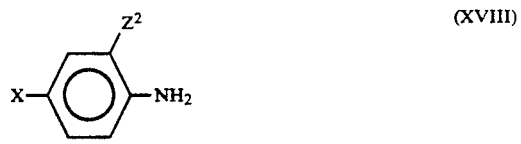

(XVIII)

wherein X and $Z^2$ have the meaning described above in connection with formula (I) (which primary amine starting material in the below-stated equation will be designated $ArNH_2$ for the sake of convenience) is subjected to the diazotization reaction:

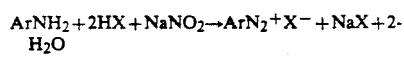

wherein X may be $Cl^-$, $Br^-$, $NO_3^-$, $HSO_4^-$, $BF_4^-$ and the like, as is conventional. The resultant diazonium salt is then coupled to an aryl compound of the formula:

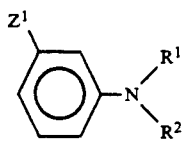

(XIX)

wherein $Z^1$, $R^1$ and $R^2$ have the meaning described above in connection with formula (I) (which for the sake of convenience will be designated $HArNR_2$ in the equation set forth below) to form the desired azo compound:

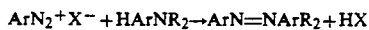

$$ArN_2^+X^- + HArNR_2 \rightarrow ArN=NArR_2 + HX$$

These reactions are conventional. Purification of the resultant products, if desired, follows procedures conventionally employed for azo dyes obtained by the above described reaction scheme. The starting primary amines of formula (XVIII), above, and the aryl compounds of formula (XIX), above, are, for the most part, known compounds made by well-known procedures; to the extent that they have not been previously described in the literature, their preparation also follows well-known procedures with which those skilled in the art are familiar. The preparation of exemplary preferred starting materials, and their coupling by the above described reactions are illustrated in greater detail in the examples provided herein.

Novel monomer structures include:

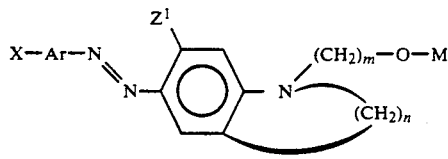

(XX)

wherein X; Ar; $Z^1$; and m have the meaning given to them in connection with formula (I), above, and n is an integer of from about 2 to 4.

In these compounds, when m is larger than 6, the monomer and, hence, the polymer produced from it has liquid crystalline properties.

These novel monomers can be prepared by the following, schematically outlined general procedure:

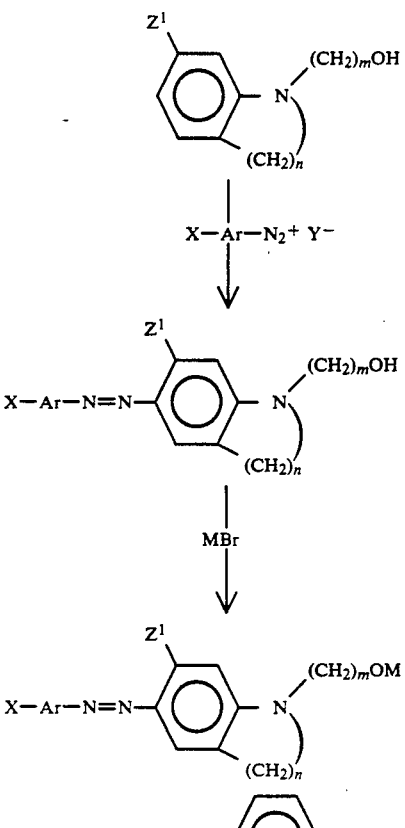

$Y^- = Cl^-$, $HSO_4^-$, $CF_3SO_3^-$, $CH_3\text{-}\!\!\bigcirc\!\!\text{-}SO_3^-$,
$PF_6^-$, $CH_3SO_3^-$ and the like.
$Z^1$ = protected Z, e.g., $CH_3C(O)NH-$, $CH_3C(O)O-$, and the like.

As previously stated, monomers of formula (I), above, wherein $R^1$ is terminally unsaturated, including the novel monomers of formula (XX), above, can be homopolymerized or copolymerized with a number of comonomers under radical or group transfer polymerization conditions. Suitable comonomers include methyl or alkyl methacrylate, methyl or alkyl acrylate, methacrylamide, acrylamide, styrene, or substituted styrene. The following exemplary reaction scheme wherein Ar, m, X and n have the aforestated meanings, illustrates an exemplary general procedure of making the present invention polymers:

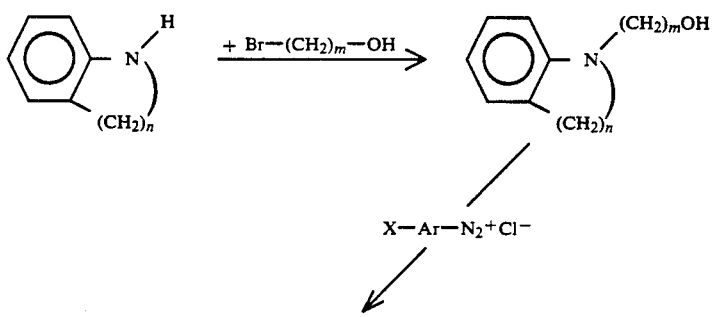

-continued

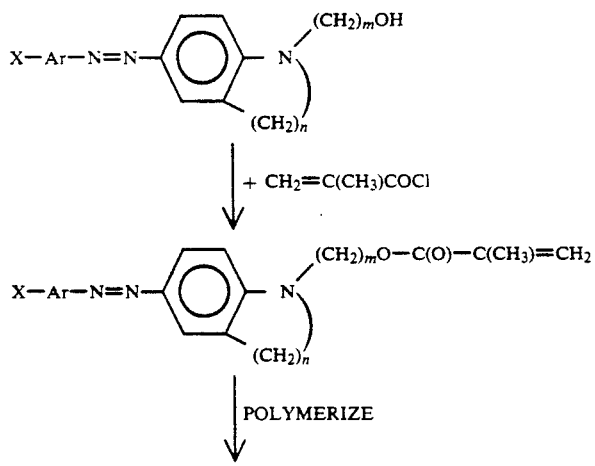

+ CH$_2$=C(CH$_3$)COCl

POLYMERIZE

An alternative route to the polymer compositions of this invention involves incorporating the indoline, 1,2,3,4-tetrahydroquinoline or alkylaniline structure in a polymer chain and then reacting the polymer with a stable aryl diazonium salt of organic superacids under homogeneous conditions. Novel stable aryl diazonium salts of organic superacid can be prepared in anhydrous organic solvents. Heterogeneous diazonium coupling of certain aryl diazonium salts of inorganic acids was reported [M. L. Schilling et al., J. Org. Chem., 53, (1988), 5538]. However, a homogeneous condition is essential for complete coupling reaction to take place and to minimize side reactions. This alternate route is described and claimed in commonly assigned, copending Appl. Ser. No. 07/456,419, now U.S. Pat. No. 5,036,142, filed of even date herewith by Chengjiu Wu, for "Process for Making Electro-Optically Active Polymers".

The above described compounds and polymers are suitable for making light modulator devices having enhanced effectiveness. For example, compounds can be doped into a polymer substrate such as polymethyl methyacrylate, polystyrene, or polycarbonate to produce polymeric films which, after acquiring a non-centrosymmetric orientation by an external field, exhibit high electro-optical responses.

The above-mentioned polymers can be dissolved in a suitable solvent such as diglyme, N,N-dimethyl formamide or acetamide and distributed by traditional coating methods such a spin-coating or dip-coating onto a suitable substrate to form polymeric thin films which, after acquiring a non-centrosymmetric orientation of these transducers by an external field, exhibit high electro-optical response.

In general, electro-optic materials may be utilized to provide an interface between electrical and optical information. Thus electro-optic materials may be used in a variety of ways to alter the propagation of a beam of light. Examples include electro-optic lenses and electro-optic deflectors. Of particular interest is the use of electro-optically active materials in optical waveguides wherein light is modified or changed as it passes through a region in which it is confined by appropriate index of refraction variations.

Important types of changes include rotation or alteration of the state of optical polarization, modulation of the amplitude of the optical intensity, modulation of the phase of the optical radiation, alteration of the directional characteristics of the radiation, and alteration of the frequency (or wavelength) of the radiation. By altering the properties of the radiation within a waveguide or a waveguide region, it is possible to encode and decode information and to route it as desired.

Non-linear optical materials can be utilized in devices which exploit their higher order responses to incident radiation. These responses include non-linear refractive index changes, frequency alteration and non-linear absorption coefficients. For frequency alteration processes such as second harmonic generation (frequency doubling) it is required that the non-linear material be non-centrosymmetric. This type of structure can be achieved by poling polymers with non-linear optical transducers. Examples of important non-linear optical devices are power limiters, harmonic generators, all optical switches and non-linear optical waveguide switches.

Electro-optically active materials provide the capability for using electric signals to change or alter the propagation of light within a medium. Of particular interest are devices which provide for external control of light within an optical waveguide through the application of an electric field. Examples of such devices and design criteria for some of these devices are known to those skilled in the art. Examples include amplitude modulators, phase modulators, Mach-Zehnder interferometers, and evanescent switches.

In one embodiment of the electro-optic effect in materials to effect amplitude modulation of light, a rectangular waveguide of width a, height b, and length L is fabricated on a substrate between two planar electrodes on the substrate separated by gap of width d with $L>d>a, b$. The material is characterized by electro-optic coefficients $r_{33}$ and $r_{13}$ so that the refractive index change parallel to the substrate induced by an electric field parallel to the substrate is $\Delta n_1 = -(\frac{1}{2})n_1^3 r_{13} E_3$. If a voltage V is applied across the waveguide is approximately $E_3 = V/d$. Monochromatic optical radiation of incident intensity, $I_0$, is coupled into the waveguide with linear polarization at ($+45°$) to the plane of the substrate. The presence of the electric field $E_3$ induces a relative phase shift as the light travels through the guide given by $\Delta\phi = 2\pi L (\Delta n_3 - \Delta n_1)/\lambda_o$ where $\lambda_o$ is the vacuum wavelength of the light. Thus the phase shift is approximately $\Delta\phi = (\pi L/\lambda_o)(n_3^3 r_{33} - n_1^3 r_{13})(V/d)$. The radiation passes through a polarizer set at approximately ($-45°$) to the plane of the substrate. For single mode propagating within the waveguide the transmitted intensity is $I=I_0\sin^2(\Delta\phi/2)$. Thus it is seen that when no voltage is applied to the device (V=0) that phase shift is zero and the transmitted intensity is zero. However, application of a voltage V will result in a finite phase shift whose magnitude is dependent upon the magnitude of the electro-optic coefficients $r_{33}$ and $r_{13}$. When the voltage for which the phase shift $\pi$ is applied ($V_\pi$), the incident radiation is completely transmitted. If more than one mode of the waveguide is exited, then full modulation may not be achieved since each mode may have a slightly different effective refractive index. Thus by applying a voltage of $V_\pi$ full modulation of the radiation can be accomplished. Since the electrical charge required to achieve voltage V is proportional to the dielectric constant of the electro-optic material $\epsilon_{33}$, and since it is important to accomplish the largest phase shift with the minimum electrical charge, a figure of merit for this device is $(n_3^3 r_{33} - n_1^3 r_{13})/\epsilon_{33}$. For LiNbO$_3$, this figure of merit is about 1.5 pm/V. For the polymeric materials of this invention with $r_{13}=r_{33}/3$ and with $n=1.5$, $r_{33}=20$ pm/V, and $\epsilon_{33}=3$, the figures of merit of about 15 pm/V are achievable with materials of this invention. Thus the polymers of this invention provide for an order of magnitude improvement in the operation of this device over the prior art inorganic devices.

The following examples further illustrate the invention and set forth the best mode presently contemplated for its practice. They are not to be interpreted in a limiting sense; the scope of the invention is limited by the appended claims.

EXAMPLE 1

Preparation of N-2-hydroxyethyl indoline

To a stirred mixture of 24 parts of indoline and 83 parts of powdered anhydrous potassium carbonate in 150 parts of acetonitrile was added 50 parts of 2-bromoethanol. The mixture was gradually warmed to reflux and kept at reflux temperature for 8 hours. The mixture was filtered and the solvent was removed. The product was purified by column chromatography on a silica gel column. The eluents were 1:1 mixture of hexane with methylene chloride and then ethyl acetate. The product was 29 parts with a boiling point of 118° C. at 0.5 torr. Proton and carbon-13 NMR spectra were consistent with structure.

EXAMPLE 2

Preparation of N-ω-hydroxyhexyl indoline

Following the general procedure in Example 1, from 21 parts of indoline, 50 parts of potassium carbonate, 150 parts of acetonitrile and 30 parts of 6-bromohexanol was obtained 29 parts of pure product. NMR spectra were consistent with structure.

EXAMPLE 3

Preparation of

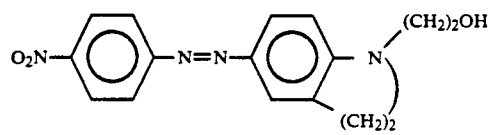

A chilled solution of 14 parts of 4-nitroaniline, 30 parts of concentrated hydrochloric acid and 100 parts of water was diazotized with 7.6 parts of sodium nitrite in 15 parts of water. The diazonium mixture was added to a stirred mixture containing 16.3 parts of N-2-hydroxyethyl indoline in 100 parts of methanol, 200 parts of water and 100 parts of crushed ice. After 1 hour, a saturated aqueous solution of 100 parts of sodium acetate was added. The mixture was stirred for 12 hours while the temperature of the mixture raised from 5° C. to room temperature. The precipitate was filtered, washed with water, dried at 80° C. in vacuum to give 24.3 parts of product which showed one spot on TLC; proton NMR was consistent with structure (δ, ppm, in CDCl$_3$): 8.0-8.2, m, 2H; 7.4-7.6, m, 4H; 6.5, m, 1H; 4.8, m, 1H (disappears upon addition of D$_2$O); 2.8-3.8, m, 8H. UV in acetonitrile: λ max 510 nm; A, 44,800.

EXAMPLE 4

Preparation of

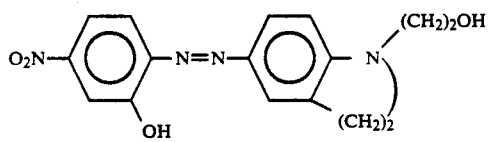

A chilled solution of 19.3 parts of 2-amino-5-nitrophenol in 32 parts of concentrated hydrochloric acid and 50 parts of water was diazotized with 9 parts of sodium nitrite in 20 parts of water. To this diazonium salt slurry was added 22 parts of N-2-hydroxethyl indoline in 50 parts of methanol. The mixture was stirred overnight while the temperature was raised from 5° C. to room temperature. The precipitate was filtered, washed with water and dried at 50° C. under vacuum, then chromatographed on a silica gel column and eluted first with 1:1 mixture of ethyl acetate and methylene chloride and then with ethyl acetate to give 10.5 parts of pure product. Proton NMR is consistent with structure (δ, ppm, in DMSO-d$_6$): 11.7, broad S, 1H; 7.4-7.9, m, 5H; 6.7, d, 1H, J=10Hz; 4.9, broad s, 1H; 3.0-4.1, m, 8H.

EXAMPLE 5

Preparation of

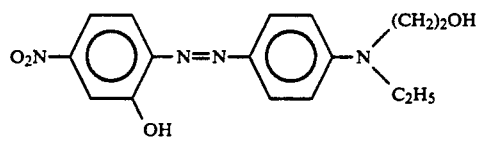

Following the procedure as Example 4, N-ethyl-N-2-hydroxyethyl aniline was used instead of N-2-hydroxyethyl indoline. Proton NMR was consistent with the assigned structure of product (δ, ppm, in DMSO-d$_6$): 11.5, br.s, 1H; 7.86, d. 2H, J=4.5Hz; 7.76, m, 3H; 6.9, d, 2H, J=4.5Hz; 4.44, br.s 1H; 3.6, m, 6H; 0.96, t, 3H, J=3.5Hz.

EXAMPLE 6

Preparation of

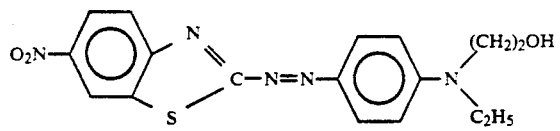

Nitrosyl sulfuric acid was prepared by mixing 7.6 parts of sodium nitrite with 50 parts of sulfuric acid at 0° C. and slowly warming up the stirred mixture to 70° C. until homogeneous. The nitrosyl sulfuric acid was added to a chilled mixture of 350 parts of glacial acetic acid and 50 parts of propionic acid. To this solution was added 19.5 parts of 2-amino-6-nitro-benzothiazole. The solution was stirred at 10° C. for 2 hrs. This diazonium mixture was added to a stirred mixture containing 16.6 parts of N-ethyl-N-2-hydroxyethyl aniline in 300 parts of methanol, 300 parts of ice water and 100 parts of crushed ice. After stirring at room temperature for 1 hr., the precipitate was filtered, washed with water and dried at 100° C. in vacuum to give 15 parts of product. The proton NMR was consistent with the assigned structure ($\delta$, ppm, in (DCl$_3$)): 8.80, d, 1H, J=1Hz; 8.16, dd, 1H, J=9, 2H, 7.93, d, 1H, J=9Hz; 7.73, d, 2H, J=9Hz; 6.96, d, 2H, J=9Hz; 6.03, br.s., 1H; 3.60, m, 6H; 1.12, t, 3H, J=6Hz. UV in acetonitrile: $\lambda$max 547 nm, A 45,900.

EXAMPLE 7

Preparation of

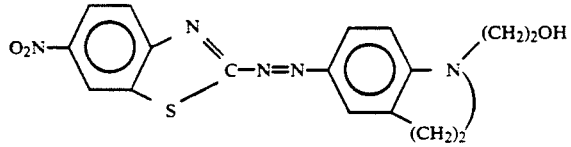

Following the procedure of Example 6, from 17 parts of N-2-hydroxyethyl indoline instead of N-ethyl-N-2-hydroxyethyl aniline was obtained 9.8 parts of product, proton NMR of which was consistent with the assigned structure.

EXAMPLE 8

Preparation of

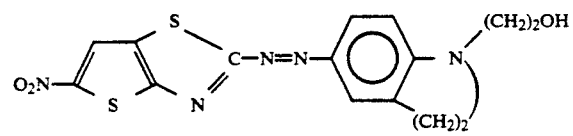

Following the same procedure of Example 6, from the reaction of the diazonium salt of 2-amino-5-nitro-thienothiazole with N-2-hydroxyethyl indoline the above product is obtained, its proton NMR is consistent with the assigned structure.

EXAMPLE 9

Preparation of

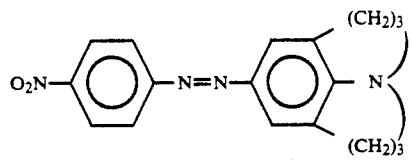

Following the general procedure of Example 3, julolidine was used instead of 2-hydroxyethyl indoline. Proton NMR of the produce was consistent with the assigned structure.

EXAMPLE 10

Preparation of

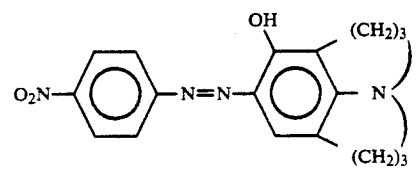

Following the procedure of Example 3, 8-hydroxyjulolidine was used instead of 2-hydroxyethyl indoline. Proton NMR of product was consistent with structure ($\delta$, ppm, in CDCl$_3$): 16.5, s, 1H, 8.26, d, 2H, J=10Hz; 7.54, d. 2H, J=10Hz; 6.80, s. 1H; 5.40, t, 4H, J=6Hz; 2.74, t, 4H, J=7Hz; 1.8-2.2, m, 4H.

EXAMPLE 11

Preparation of

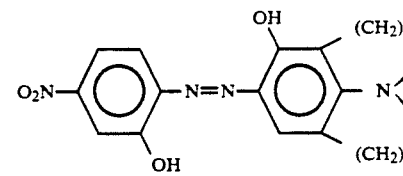

To a solution of 1.9 parts of 8-hydroxyjulolidine in 10 parts of N,N-dimethylformamide at 0° C. was added 3.8 parts of 2-hydroxy-4-nitro-benzene diazonium tosylate (Example 48, 1.2 equivalent) in 10 parts of N,N-dimethylformamide. After stirring for 3 hrs. while the temperature was raised to room temperature, the mixture was poured into 100 parts of ice water. The precipitate was filtered, washed with water and dried at 80° C. in vacuum to give 3.0 parts of almost pure product. Its proton NMR was consistent with structure.

Utilizing the procedure of Example 11, 2-hydroxy-5-nitrobenzene diazonium tosylate can be reacted with various indolines to obtain electro-optically active compounds of this invention. Exemplary suitable starting indolines and the resultant products are listed below:

a) Starting indoline 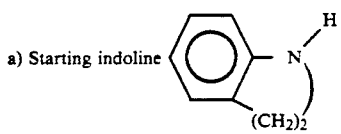

Product (a):

-continued

O₂N—⌬(OH)—N=N—⌬—N(H)(CH₂)₂ b) Starting indoline: ⌬—N(CH₃)(CH₂)₂

Product (b): O₂N—⌬(OH)—N=N—⌬—N(CH₃)(CH₂)₂ c) Starting indoline: ⌬—N(C(CH₃)₃)(CH₂)₂

Product (c): O₂N—⌬(OH)—N=N—⌬—N(C(CH₃)₃)(CH₂)₂ d) Starting indoline: ⌬—N(cycloC₆H₁₁)(CH₂)₂

Product (d): O₂N—⌬(OH)—N=N—⌬—N(cycloC₆H₁₁)(CH₂)₂

EXAMPLE 12

Preparation of

O₂N—⌬—N=N—⌬(OH)—N((CH₂)₃)((CH₂)₃)

Following the procedure in Example 11, from 1.7 parts of julolidine was obtained 3.0 parts of product, the proton NMR spectrum of which was consistent with the structure.

EXAMPLE 13

Preparation 2-N-indolinoethyl methacrylate

Method A

To a stirred mixture containing 10 parts of 2-hydroxyethyl indoline, 11 parts of triethylamine and 100 parts of methylene chloride was slowly added 10 parts of methacryloyl chloride at room temperature. After 8 hrs., 100 parts of saturated aqueous sodium bicarbonate was added to the mixture. The organic phase was separated, washed with water and dried over anhydrous calcium chloride. By chromatography using a silica gel column and 80 percent hexane—20 percent ethyl acetate as eluent, 8.5 parts of pure product was obtained; proton and carbon-13 NMR spectra were consistent with structure.

The procedure Method A can conveniently be utilized to prepare other compounds of the present invention. For example, following this procedure, 2-chloroethylvinylether and

O₂N—⌬—N=N—⌬—N(H)(CH₂)₂ can be reacted to form

O₂N—⌬—N=N—⌬—N((CH₂)₂—O—CH=CH₂)((CH₂)₂)

as the desired product, or vinylbenzyl chloride (mixture of p- and m- isomers) can be reacted with

O₂N—⌬—N=N—⌬—N((CH₂)₂—OH)((CH₂)₂)

to obtain

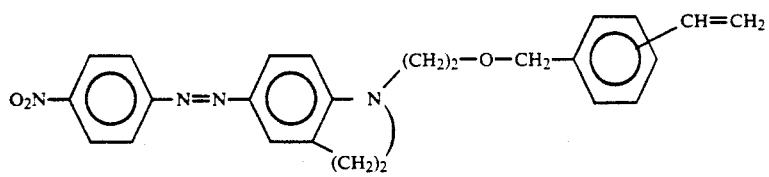

or epibromohydrin can be reacted with the compound prepared in Example 3 to obtain

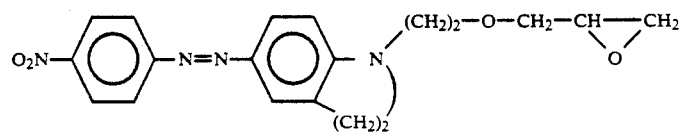

Also, this method can be used to prepare, for example, bifunctional monomers from the compound obtained in Example 5, by treating this compound with various reactants as set forth below:

a) Reactant: $CH_2=CH-COCl$

Product (a)

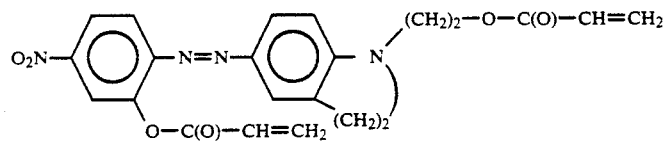

b) Reactant: $CH_2\underset{\underset{O}{\diagdown\diagup}}{\text{———}}CH-CH_2Cl$ Product (b)

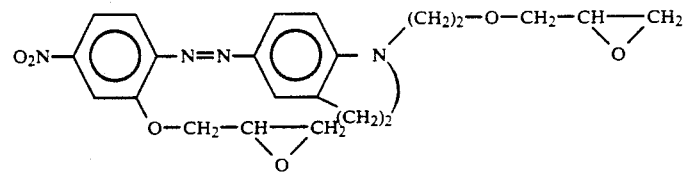

c) Reactant: $CH_2=CH-\phantom{x}\!\!\!\!\bigcirc\!\!\!\!\phantom{x}-CH_2Cl$ (mixture of p- and m- isomers)

Product (c)

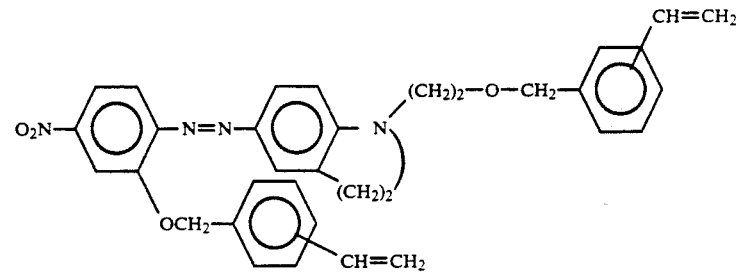

d) Reactant: $CH_2=CHOCH_2CH_2Cl$

Product (d)

-continued

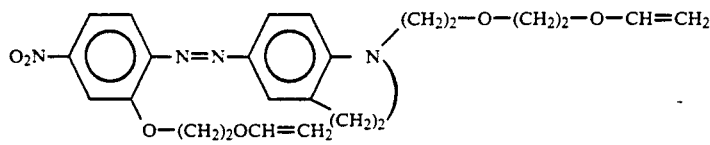

Method B

To a mixture containing 1.2 parts of indoline, 1.1 parts of anhydrous potassium carbonate and 10 parts of acetonitrile was added 1.8 parts of 2-bromoethyl methacrylate. The mixture was refluxed for 8 hours. After chromatography on a silica gel column, 1.4 parts of the above product was obtained.

EXAMPLE 14

Preparation of

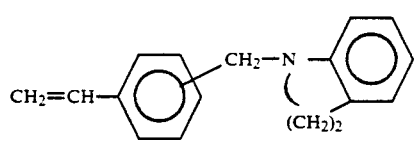

To a stirred mixture containing 10 parts of indoline, 11 parts of triethylamine and 100 parts of methylene chloride is added 10 parts of vinylbenzylchloride (mixture of p- and m-isomers). After liquid chromatography the above moment is obtained.

EXAMPLE 15

Preparation of 2-N-indolinoethyl acrylate

Following the procedure in Example 13, Method A, from 10 parts of acryloyl chloride was obtained 7 parts of pure product after liquid chromatography.

EXAMPLE 16

Preparation of

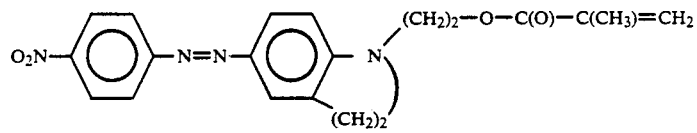

Following the procedure in Example 13, Method A, from 20 parts of the compound prepared in Example 3 instead of 2-hydroxyethyl indoline was obtained 12.5 parts of pure product after chromatography, its proton NMR was consistent with the assigned structure.

EXAMPLE 17

Preparation of

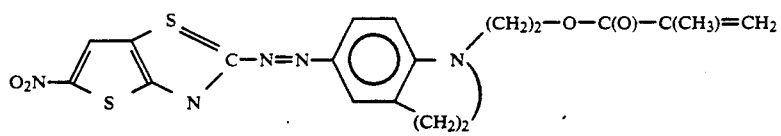

Following the procedure in Example 13, Method A, from 7 parts of the compound prepared in Example 7 was obtained 3.5 parts of pure product after chromatography on a silica gel column using 1:1 mixture of methylene chloride and ethyl acetate as eluent. Proton NMR of the product was consistent with the assigned structure.

EXAMPLE 18

Preparation of

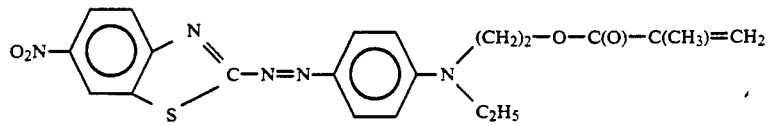

Following the procedure in Example 13, Method A, from the reaction of the alcohol prepared in Example 8 with methacryloyl chloride is obtained the above product, its structure is confirmed by proton NMR.

EXAMPLE 19

Preparation of

Following the procedure in Example 13, Method A, from 25 parts of the compound prepared in Example 6 was obtained 13.5 parts of pure product after chromatography on a silica gel column using a 1:1 mixture of ethylacetate and methylene chloride as eluent. Proton NMR of the product was consistent with the assigned structure (δ, ppm, in CDCl₃): 8.69, d, 1H, J=2Hz, 8.29, dd, 1H, J=9, 2Hz; 8.07, d, 1H, J=9Hz; 7.85, d, 2H, J=9.2Hz; 6.66, d, 2H, J=9.2Hz; 6.17, s, 1H; 5.66, m, 1H, J=1.5Hz; 4.47, t, 2H, J=5.0Hz; 3.82, t, 2H, J=5.0Hz; 3.58, t, 2H, J=6.6Hz; 1.98, m, 3H, J=1.5Hz; 1.32, t, 3H, J=6.6Hz.

EXAMPLE 20

Preparation of $$O_2N-\text{Ar}-N=N-\text{Ar}-N \begin{array}{l} (CH_2)_2-O-C(O)-C(CH_3)=CH_2 \\ C_2H_5 \end{array}$$

O—C(O)—C(CH₃)=CH₂

Following the procedure in Example 13, Method A, from 18 parts of the compound prepared in Example 5 there was obtained two compounds after chromatography on a silica gel using a 70:30 mixture of hexane and acetone as eluent. The first fraction was 16.5 parts of the title product, proton NMR of which is consistent with the assigned structure (δ, ppm, in CDCl₃): 8.1–8.3, m, 2H; 7.7–8.0, m, 3H; 6.7–7.0, m, 2H; 6.53; broad S, 1H; 6.17, broad S, 1H; 5.83, m, 1H; 5.66, m, 1H; 4.3–4.6, t, 2H; 3.4–3.9, m, 4H; 2.20, s, 3H; 1.98, s, 3H; 1.3, t, 3H. The second fraction consisted of 6.0 parts of:

$$O_2N-\text{Ar}-N=N-\text{Ar}-N \begin{array}{l} (CH_2)_2OH \\ C_2H_5 \end{array}$$

O—C(O)—C(CH₃)=CH₂

EXAMPLE 21

Preparation of $$O_2N-\text{Ar}-N=N-\text{Ar}-N \begin{array}{l} (CH_2)_2-O-C(O)-C(CH_3)=CH_2 \\ (CH_2)_2 \end{array}$$

O—C(O)—C(CH₃)=CH₂

Following the general procedures of preparing 13, Method A, from 3.3 parts of the compound prepared in Example 4, 2.2 parts of triethylamine and 2.6 parts of methacryloyl chloride, there was obtained 3.5 parts of product. Its proton NMR spectrum was consistent with the assigned structure.

EXAMPLE 22

Polymer of 2-N-indolinoethyl methacrylate

A solution of 12 parts of 2-N-indolinoethyl methacrylate, prepared in Example 13, and 0.046 part (0.2 mole percent of monomer) of 2,2'-azobis(2,4-dimethyl-4-methoxyvaleronitrile) in 35 parts of N,N-dimethyl-formamide was stirred under an inert atmosphere at 30° C. for 48 hrs. The reaction mixture was poured into methanol to precipitate 9.7 parts of polymer. The thermoplastic polymer has a weight average molecular weight of about 100,000 and a T_g of 56° C.

EXAMPLE 23

Polymer of 2-N-(N-ethylanilino)ethyl methacrylate

Following the general procedure of Example 22, from 20 parts of 2-N-(N-ethylanilino)ethyl methacrylate and 0.053 part of 2,2'-azobis(2,4-dimethyl-4-methoxyvaleronitrile) (0.2 mole percent of monomer) there was obtained 15.3 parts of polymer. The polymer had a weight average molecular weight of about 110,000 and a T_g of 50° C.

EXAMPLE 24

Copolymer of 2-N-indolinoethyl methacrylate with methyl methacrylate

Following the general procedure of Example 22, from 8.7 parts of a monomer mixture containing 50 mole percent of 2-N-indolinoethyl methacrylate and 50 mole percent of methyl methacrylate, there was obtained 7.0 parts of a copolymer which contained 53 mole percent of 2-N-indolinoethyl methacrylate unit. The thermoplastic copolymer had a weight average molecular weight of about 120,000 and a T_g of 67° C.

EXAMPLES 25–28

Following the general procedure of Example 24, monomer mixtures containing various mole percents of 2-N-indolinoethyl methacrylate and methyl methacrylate were copolymerized to obtain copolymers which contained various amounts of 2-N-indolinoethyl methacrylate units. The results are summarized in Table I below.

TABLE I

Copolymers of 2-N-Indolinoethyl Methacrylate (IM) with Methyl Methacrylate (MM)

| Ex. | IM in Monomer (Mole %) | IM in Polymer (Mole %) | Wt. Avg. Mol. Wt. × 10³ | T_g(°C.) |
|---|---|---|---|---|
| 25 | 20 | 19 | 157 | 95 |
| 26 | 40 | 38 | 125 | 78 |
| 27 | 60 | 65 | 120 | 65 |
| 28 | 80 | 75 | 110 | 57 |

EXAMPLE 29–32

Following the general procedure of Example 24 monomer mixtures containing various mole percents of 2-N-(N-ethylanilino)ethyl methacrylate and methyl methacrylate were copolymerized to obtain copolymer containing various mole percents of the 2-N-(N-ethylanilino)ethyl methacrylate unit. The results are summarized in Table II below.

TABLE II

Copolymers of 2-N-(N-ethylanilino)ethyl Methacrylate (EEM) with Methyl Methacrylate (MM)

| Ex. | EEM in Monomer (Mole %) | EEM in Polymer (Mole %) | Wt. Avg. Mol. Wt. × $10^3$ | $T_g$(°C.) |
|---|---|---|---|---|
| 29 | 20 | 17 | 150 | 85 |
| 30 | 40 | 40 | 140 | 66 |
| 31 | 60 | 54 | 135 | 55 |
| 32 | 80 | 76 | 130 | 45 |

EXAMPLES 33-38

Copolymer of

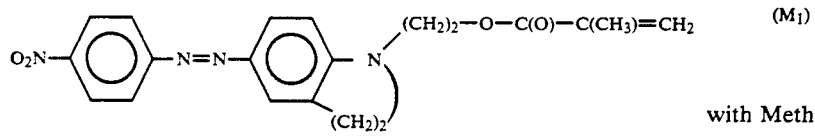
(M₁)

with Methyl Methacrylate

Following the general procedure of Example 24, monomer mixtures containing various mole percents of monomer prepared in Example 16, methyl methacrylate and 0.1 mole percent of 2,2'-azobis(2,4-dimethyl-4-methoxyvaleronitrile), were copolymerized to obtain the corresponding copolymers. The results are summarized in Table III below.

TABLE III

| Ex. | M₁ in monomer (mole %) | $T_g$(°C.) |
|---|---|---|
| 33 | 10 | 134 |
| 34 | 20 | 135 |
| 35 | 30 | 133 |
| 36 | 40 | 135 |
| 37 | 60 | 137 |
| 38 | 80 | 134 |

EXAMPLE 39

Polymer of

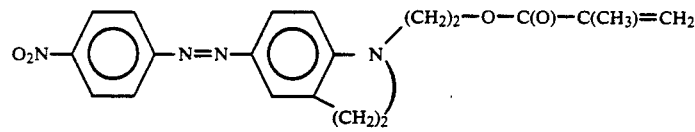

Following the general procedure of Example 22, from 8.8 parts of a monomer prepared in Example 16, and 0.3 mole percent of 2,2'-azobis(2,4-dimethyl-4-methoxyvaleronitrile) was obtained 1.0 part of a polymer which has a $T_g$ of 137° C.

EXAMPLE 40

Polymer of 2-N-indolinoethyl acrylate

Following the general procedure of Example 22, from 8.5 parts of 2-N-indolinoethyl acrylate prepared in Example 15 and 0.2 mole percent of 2,2'-azobis(2,4-dimethyl-4-methoxyvaleronitrile) was obtained 3.0 parts of a soft polymer.

EXAMPLES 41-43

Copolymers of (M₂)

with Methyl Methacrylate

Following the general procedure of Example 24, monomer mixtures containing various mole percents of monomer prepared in Example 19, methyl methacrylate and 0.1 mole percent of 2,2'-azobis(2,4-dimethyl-4-methoxyvaleronitrile) was copolymerized to obtain the corresponding copolymers. The results are summarized in Table IV below.

TABLE IV

| Ex. | M₂ in monomer (mole %) | Wt. Avg. Mol. Wt. of copolymer × $10^3$ | $T_g$(°C.) |
|---|---|---|---|
| 41 | 10 | 50 | 139 |
| 42 | 20 | 50 | 145 |
| 43 | 40 | 50 | 150 |

EXAMPLE 44

Copolymer of

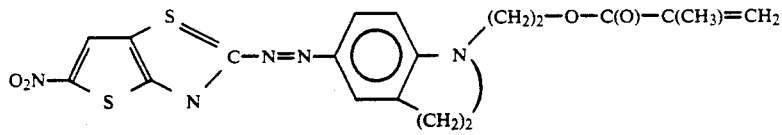

with Methyl Methacrylate

Following the general procedure of Example 24, from 4.2 parts of a monomer mixture containing 20 mole percent of monomer prepared in Example 18 and 80 mole percent of methyl methacrylate and 0.1 mole percent of 2,2'-azobis(2,4-dimethyl-4-methoxyvaleronitrile) there was obtained 1.0 parts of a copolymer.

EXAMPLE 45

Polymerization of

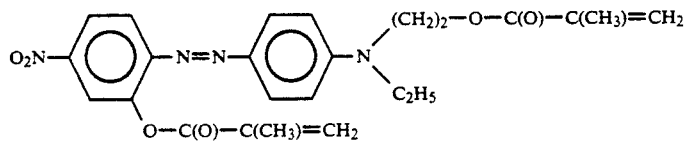

A vacuum de-gassed solution containing 1 part of the monomer prepared in Example 20 and 0.01 part of 2,2'-azobis(2,4-dimethyl-4-methoxyvaleronitrile) in 10 parts of dimethyl formamide was stirred in a water bath at 30+0.1° C. for 12 hrs. to form a gel. The gel was thoroughly washed with methanol to remove solvent and monomer and gave 0.2 part of an insoluble polymer which does not show a $T_g$ transition up to its decomposition temperature at 250° C.

EXAMPLE 46

Photo-crosslinking of

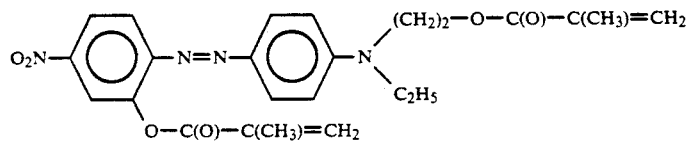

A film of the bifunctional monomer prepared in Example 20 is doctor bladed onto a quartz substrate. A thin stripe of actinic radiation from a xenon lamp is applied to the film via a masked exposure. After exposure the crosslinked material in the exposed region is no longer soluble in a solvent for the monomer which is used to wash away the unexposed portions of the film. The result is a free-standing rib waveguide which guides optical radiation at 810 nm.

EXAMPLE 47

Orientation and photo-crosslinking of

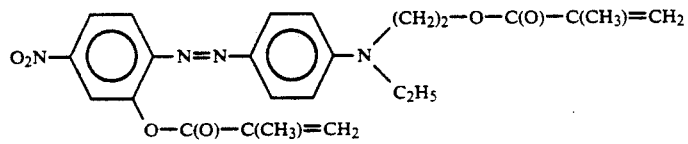

A film of the bifunctional monomer prepared in Example 20 is doctor bladed onto a quartz substrate bearing two aluminum electrode pads which are separated by 100 microns. The film is exposed to actinic radiation from a xenon lamp and optionally heated while a high DC voltage is established between the pad electrodes. When the film is polymerized and cooled the voltage is removed. The sample is used to frequency double a 1.064 micron laser beam which is directed perpendicular to the film into the gap between the pad electrodes.

EXAMPLE 48

Preparation of 2-hydroxy-4-nitrobenzenediazonium tosylate

Five parts of 2-amino-5-nitro-phenol and 12.5 parts of p-toluene sulfuric acid monohydrate were dissolved in 300 parts of methanol and then diazotized and 3.9 parts of isoamyl nitrite. The solution was filtered and the filtrate was poured into 700 parts of ethyl ether. The precipitate was collected, washed with ethyl ether and dried under vacuum to give 7.7 parts of 2-hydroxy-4-nitrobenzenediazonium tosylate with purity >95%.

EXAMPLE 49

Preparation of 4-cyanobenzenediazonium tosylate

Following the procedure in Example 48, from 2.3 parts of 4-aminobenzonitrile and 4 parts of p-toluenesulfonic acid monohydrate was obtained 4.3 parts of pure 4-cyanophenyldiazonium tosylate.

EXAMPLE 50

Preparation of 2-hydroxy-4-carbomethoxybenzene diazonium tosylate

Following the procedure in Example 48, from 1.7 parts of methyl 4-amino-3-hydroxyl benzoate and 3.8 parts of p-toluenesulfonic acid monohydrate was obtained 3.1 parts of product, its proton NMR was consistent with the assigned structure.

EXAMPLE 51

Preparation of 2-hydroxy-4-carbo(n-octyl)oxybenzene diazonium tosylate

Following the procedure in Example 48, from 2.7 parts of n-octyl 4-amino-3-hydroxyl benzoate and 3.8 parts of p-toluenesulfonic acid monohydrate is obtained the above product which proton NMR is consistent with the assigned structure.

EXAMPLE 52

Preparation of 2-hydroxy-4-carbo(cyclohexyl)oxybenzene diazonium tosylate

Following the procedure in Example 48, from cyclohexyl 4-amino-3-hydroxyl benzoate the above product is obtained, which proton NMR is consistent with the assigned structure.

EXAMPLE 53

Preparation of 2-hydroxy-4-carbo(t-butyl)oxybenzene diazonium tosylate

Following the procedure in Example 48, from t-butyl 4-amino-3-hydroxyl benzoate the above product is obtained, which proton NMR is consistent with the assigned structure.

EXAMPLE 54

Preparation of 2-hydroxy-4-nitrobenzene diazonium triflate

To an ice cooled solution containing 5 parts of 2-amino-5-nitrophenol and 9.6 parts of trifluoromethane sulfonic acid in 150 parts of methanol was slowly added 3.9 parts of isoamyl nitrite to complete diazotization. The solution was filtered and the filtrate was poured into 700 parts of ethyl ether. The precipitate was collected, washed with ether and dried under vacuum to give 4.5 parts of product with purity >95%.

EXAMPLE 55

Preparation of 4-(dicyanovinyl)benzenediazonium triflate

Following the procedure in Example 54, from 4-(dicyanovinyl)aniline and trifluoromethanesulfonic acid the above product is obtained. Proton NMR is consistent with the assigned structure.

EXAMPLE 56

Preparation of 2-hydroxy-4-(dicyanovinyl)benzenediazonium triflate

Following the procedure in Example 54, from 2-hydroxy-4-(dicyanovinyl)aniline and trifluoromethanesulfonic acid the above product is obtained, proton NMR is consistent with the assigned structure.

EXAMPLE 57

Preparation of 4-(tricyanovinyl)benzenediazonium triflate

Following the procedure in Example 54, from 4-(tricyanovinyl)aniline and trifluoromethanesulfonic acid the above product is obtained, proton NMR is consistent with the assigned structure.

EXAMPLE 58

Preparation of 4-nitrobenzene diazonium triflate

Following the procedure in Example 54, from 4.5 parts of 4-nitroaniline and 9.6 parts of trifluoromethane sulfonic acid was obtained 4.6 parts of product with purity >95%.

EXAMPLE 59

Preparation of 4-nitrobenzene diazonium methylsulfonate

Following the procedure in Example 54, from 4.5 parts of 4-nitroaniline and 6.5 parts of methane sulfonic acid was obtained 5.8 parts of product.

EXAMPLE 60

Preparation of

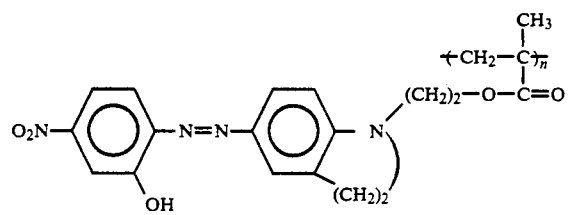

To a stirred solution of 1.5 parts of homopolymer of 2-N-indolino-ethyl methacrylate (Example 22) in 4.5 parts of N,N-dimethylformamide at $-10°$ C. was slowly added 3.5 parts (1.5 equivalents) of 2-hydroxy-4-nitrobenzene diazonium tosylate in 30 parts of N,N-dimethylformamide. After 2 hrs., the reaction mixture was poured into 500 parts of methanol. The precipitate was collected, washed with methanol and dried in vacuum to give 1.6 parts of a polymer in which the phenyl ring was 90 mole percent diazo-coupled. The polymer had a $T_g$ of 115° C. and completely dissolved in N,N-dimethylformamide. This polymer was redissolved in 20 parts of N,N-dimethylformamide and reacted with 0.8 part of 2-hydroxy-4-nitrobenzene diazonium tosylate at $-10°$ C. for 3 hrs. to give 1.5 parts of polymer which was completely coupled.

EXAMPLE 61

Preparation of

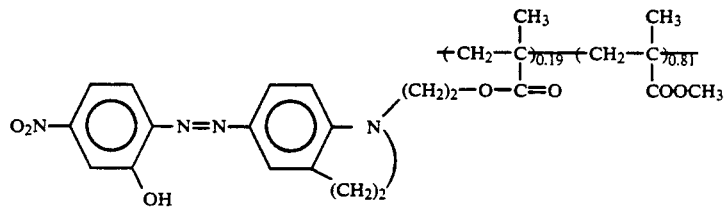

Following the general procedure of Example 60, from a copolymer containing 19 mole percent of 2-N-indolinoethyl methacrylate and 81 mole percent of methyl methacrylate (Example 25) and 2-hydroxy-4-nitrobenzene diazonium triflate (1.2 equivalents) was obtained a copolymer which was 70 mole percent diazo-coupled. Second treatment with the same diazonium salts gave copolymer almost 100 percent coupled which had a $T_g$ of 115° C.

EXAMPLE 62

Preparation of

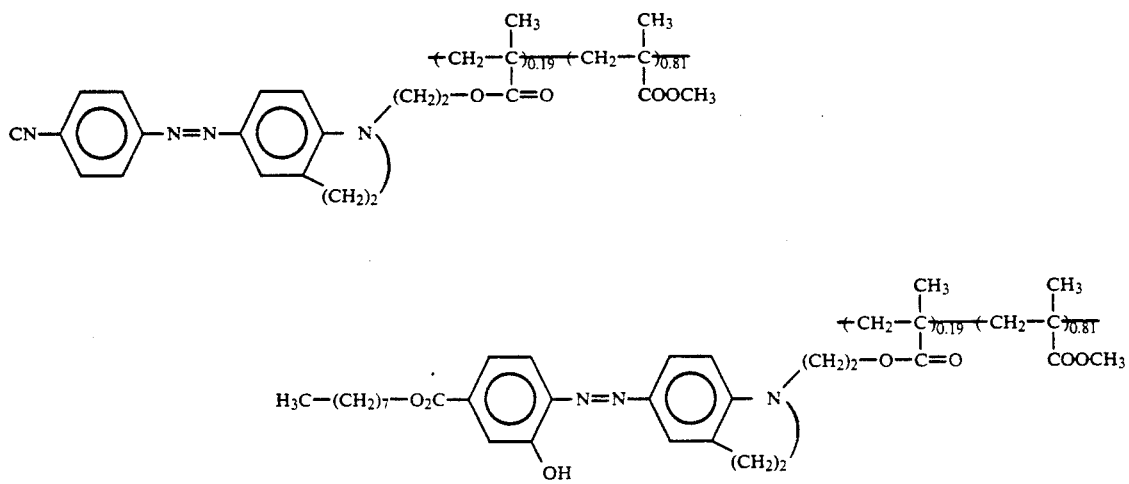

Following the general procedure of Example 60, from a copolymer containing 19 mole percent of 2-N-indolinoethyl methacrylate and 81 mole percent of methyl methacrylate (Example 25) and 4-cyanobenzenediazonium tosylate (1.3 equivalents) from Example 49 reacted at −20° C. for 64 hrs. was obtained a linear copolymer which from proton NMR was 96 mole percent diazo-coupled and had a $T_g$ of 120° C. UV max (film) of the copolymer was at 460 nm. The characteristic 2220 cm$^{-1}$ peak of cyano group was evident in IR.

EXAMPLE 63

Preparation of

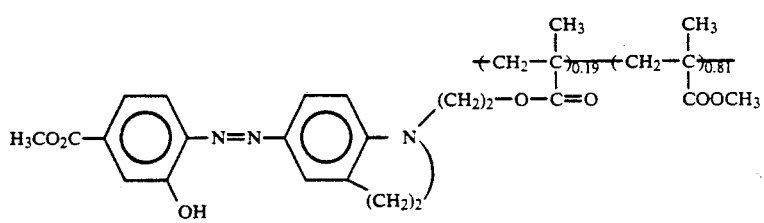

Following the general procedure of Example 60, from a copolymer containing 19 mole percent of 2-N-indolinoethyl methacrylate and 81 mole percent of methyl methacrylate (Example 25) and 2-hydroxy-4-carbomethoxybenzene diazonium tosylate (1.2 equivalents) from Example 50 reacted at −10° C. for 42 hrs. was obtained a linear copolymer which from proton NMR was almost 100 percent diazo-coupled and had a $T_g$ of 118° C.

EXAMPLE 64

Preparation of

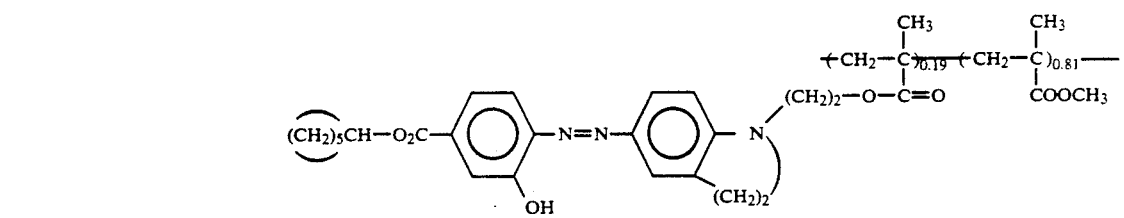

Following the general procedure of Example 60, from a copolymer containing 19 mole percent of 2-N-indolinoethyl methacrylate and 81 mole percent of methyl methacrylate (Example 25) and 2-hydroxy-4-carbo(n-octyl)oxybenzene diazonium tosylate (1.2 equivalents) from Example 51 reacted at −10° C. for 48 hrs. is obtained a linear copolymer, the proton NMR is consistent with the assigned structure.

EXAMPLE 65

Preparation of

Following the general procedure of Example 60, from a copolymer containing 19 mole percent of 2-N- indolinoethyl methacrylate and 81 mole percent of methyl methacrylate (Example 25) and 2-hydroxy-4-carbo(n-octyl)oxybenzene diazonium tosylate (1.2 equivalents) from Example 52 reacted at −10° C. for 48 hrs. is obtained a linear copolymer, the proton NMR is consistent with the assigned structure.

EXAMPLE 66

Preparation of

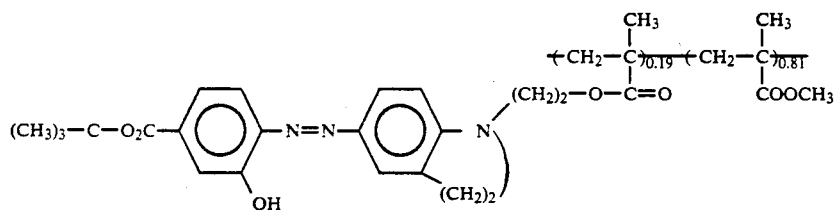

Following the general procedure of Example 60, from a copolymer containing 19 mole percent of 2-N-indolinoethyl methacrylate and 81 mole percent of methyl methacrylate and 2-hydroxy-4-carbo(t-butyl)oxybenzene diazonium tosylate (1.2 equivalents) from Example 53 reacted at −10° C. for 48 hrs. is obtained a linear copolymer, the proton NMR is consistent with the assigned structure.

EXAMPLE 67

Preparation of

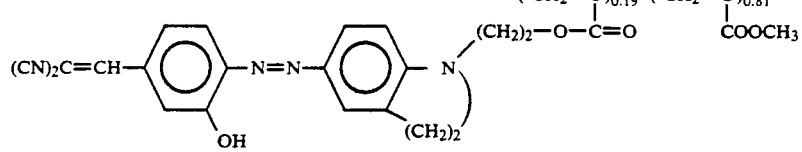

Following the general procedure of Example 60, from a copolymer containing 20 mole percent of 2-N-indolinoethyl methacrylate and 80 mole percent of methyl methacrylate (Example 25) and 4-(dicyanovinyl)benzene diazonium triflate (1.1 equivalents) from Example 55 reacted at −20° C. for 48 hrs. is obtained a linear copolymer, the proton NMR is consistent with the assigned structure.

EXAMPLE 68

Preparation of

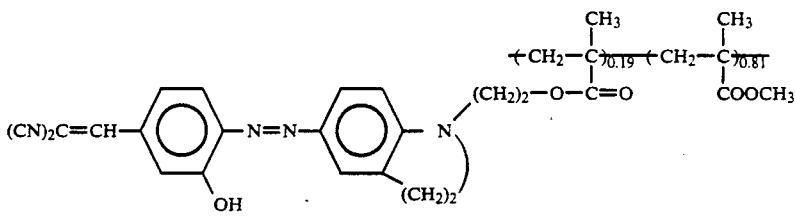

Following the general procedure of Example 60, from a copolymer containing 19 mole percent of 2-N-indolinoethyl methacrylate and 81 mole percent of methyl methacrylate (Example 25) and 2-hydroxy-4-(dicyanovinyl)benzene diazonium triflate (1.1 equivalents) from Example 56 reacted at −20° C. for 48 hrs. is obtained a linear copolymer, the proton NMR is consistent with the assigned structure.

EXAMPLE 69

Preparation of

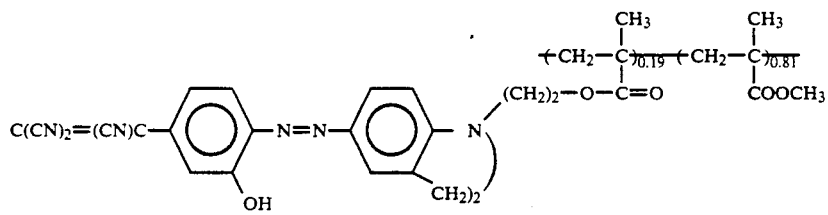

Following the general procedure of Example 60, from a copolymer containing 19 mole percent of 2-N-indolinoethyl methacrylate and 81 mole percent of methyl methacrylate (Example 25) and 4-(tricyanovinyl)benzene diazonium triflate (1.1 equivalents) from Example 57 reacted at −20° C. for 48 hrs. is obtained a linear copolymer, the proton NMR is consistent with the assigned structure.

EXAMPLE 70

Preparation of

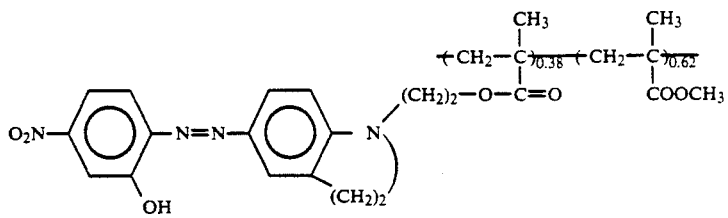

Following the general procedure of Example 60, from a copolymer containing 38 mole percent of 2-N-indolinoethyl methacrylate and 62 mole percent of methyl methacrylate (Example 26) and 2-hydroxy-4-nitrobenzene diazonium triflate (1.5 equivalents) was obtained a copolymer which was 95 mole percent diazo-coupled. Second treatment with the same diazonium salts gave copolymer almost 100 percent coupled which has a $T_g$ of 115° C.

EXAMPLE 71

Preparation of

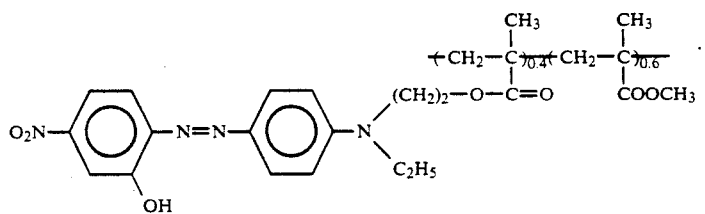

Following the general procedure of Example 60, from a copolymer containing 40 mole percent of 2-N-(n-ethylanilino)ethyl methacrylate and 60 mole percent of methyl methacrylate (Example 30) and 1.2 equivalents of 2-hydroxy-4-nitrobenzenediazonium tosyl reacted at $-10°$ C. for 48 hrs. is obtained a linear copolymer, the proton NMR is consistent with the assigned structure.

EXAMPLE 72

Preparation of

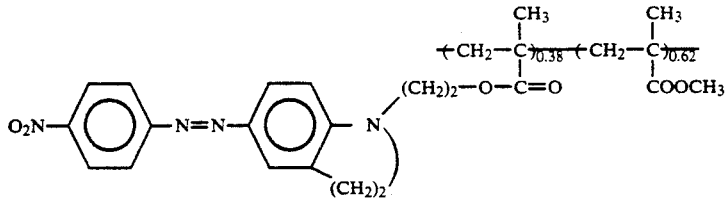

Following the general procedure of Example 60, from a copolymer containing 38 mole percent of 2-N-indolinoethyl methacrylate and 62 mole percent of methyl methacrylate (Example 26) and 1.5 equivalent of 4-nitrobenzene diazonium methyl sulfonate was obtained a polymer which was 70 mole percent diazo-coupled. Second treatment with the same diazonium salts gave a polymer which was almost 100 percent coupled and had a $T_g$ of 120° C.

EXAMPLE 73

Preparation of

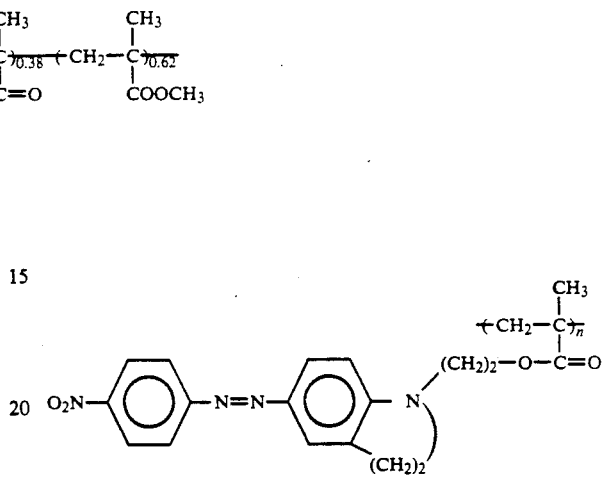

Following the general procedure of Example 60, from a homopolymer of 2-N-indolinoethyl methacrylate (Example 22) and 1.5 equivalent of 4-nitrobenzene diazonium triflate was obtained a polymer which was 78 mole percent diazo-coupled. Second treatment with the same diazonium salts gave a polymer which was almost 100 percent coupled and had a $T_g$ of 120° C.

EXAMPLE 74

Measurement of electro-optic coefficient of polymer in Example 33

A solution of three parts of diglyme to one part of a copolymer, prepared as described in Example 33, was spin coated onto a Corning 7059 glass substrate partially covered with a 300 Angstrom thick electrically conductive indium tin oxide (ITO) layer. The ITO was photolithographically defined to form slit type electrodes with dimensions of 5 mm×9 mm and a distance between the electrodes of 100 microns. The diglyme solvent was evaporated in an oven at 132° C., yielding a 2.4 micron thick solid polymer film.

The sample was placed in a vacuum chamber with the pressure reduced to $10^{-5}$ torr. Electrical connections were made to the two ITO electrodes in the vacuum chamber and the sample was heated to 132° C. A DC voltage was established between the two ITO electrodes such that the polymer in the electrode gap region experienced a static electric field strength of 0.5 MV/cm. The field was maintained until the sample was cooled to room temperature.

The sample was then mounted in a modified Senarmont compensator apparatus used for measuring the electro-optic coefficients. Details of its operation have been described [T. Yoshimura, J. Appl. Phys. 62, (1987), 2027]. A 0.81 micron diode laser was used to make all of the measurements. A phase retardation versus applied voltage measurement showed a linear relationship, establishing that the polymer was noncentrosymmetrically aligned and optically nonlinear.

Assuming the refractive index of the polymer is 1.57, and that $r_{13}=r_{33}/3$ the electro-optic coefficient $r_{33}$ was measured as:

$$r_{33}=3.5 \text{ pm/V}$$

EXAMPLES 75-77

Following the procedure in Example 74, the electro-optic coefficient of the polymer described in Examples 34, 35 and 42 were determined as follows:

Example 34: $r_{33}=6.4$ pm/V
Example 35: $r_{33}=9.0$ pm/V
Example 42: $r_{33}=4.7$ pm/V

EXAMPLE 75 COMPARATIVE

A polymeric material containing a non-planarized molecular transducer similar to that described by the prior art of composition (designated here polymer PA) was prepared using procedures analogous to those of the other examples. Polymeric compositions containing planarized molecular transducers of this invention (designated here polymer A and polymer B) with compositions were prepared as described in Examples 34 and 61. Thin films of these polymers were spin-coated upon a transparent quartz substrate affixed with metal electrodes spaced by a gap of 100 μm. The thickness of the films was in each case approximately 1 μm. The films were first poled at their glass transition temperatures (132° C. for polymer PA; 135° C. for polymer A; 115°-118° C. for polymer B) with a field of $0.5 \times 10^6$ V/cm and then cooled to room temperature in the presence of the field. Using a standard Senarmont compensator configuration, the electro-optic response for each of the three films was measured at a wavelength of 810 nm. The measured response is $n_e^3 r_{33} - n_o^3 r_{13}$ where $r_{33}$ and $r_{13}$ are standard electro-optic coefficients and where $n_e$ and $n_o$ are the refractive indices parallel and perpendicular to the direction of the poling field. A derived electro-optic coefficient, $r_{33}$, may be obtained from the measured response by assuming that $n_e = n_o$ and that $r_{33} = 3r_{13}$ as expected theoretically. The response per transducer unit, designated R, is $(n_e^3 r_{33} - n_o^3 r_{13})/X_t$ where $X_t$ is the transducer mole fraction in the polymer. The table below gives the measured response, the derived $r_{33}$, and the derived response per transducer unit R for the three polymers.

| Polymer | $X_t$ | $n_e^3 r_{33} - n_o^3 r_{13}$ (pm/V) | $r_{33}$ (pm/V) | R (pm/V) |
|---|---|---|---|---|
| PA (prior art) | 0.2 | 9.4 | 3.5 | 17.5 |
| A (this invention) | 0.2 | 18.8 | 6.4 | 32. |
| B (this invention) | 0.21 | 27.4 | 9.0 | 42.9 |

The dramatically-improved electro-optic response for the material of this invention is evident in the considerably-increased values for R [or $r_{33}$ or $(n_e^3 r_{33} - n_o^3 r_{13})$]

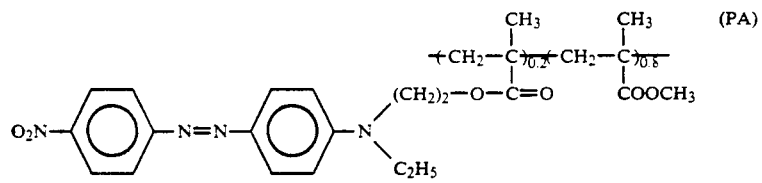

(PA)

obtained.

EXAMPLE 79 COMPARATIVE

The polymeric materials designated as polymers PA and B of Example 77 were spin-coated onto silicon

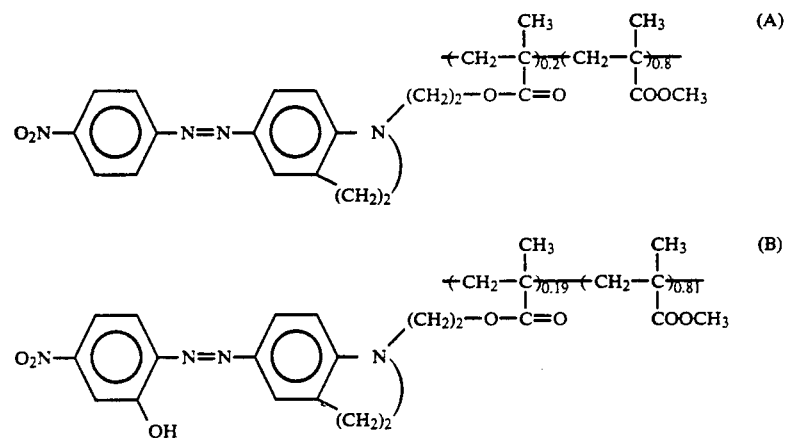

wafers and baked to give dry films. A source of polarized white light was focused to a small diameter spot, which was directed to fall onto each of the films for a period of twenty seconds. A microscope with polarized, reflecting optics was used could be easily observed on the film composed of polymer PA. This indicated that the white light had caused trans-cis isomerization around the azo linkage of the molecular transducer. This was further verified by heating the sample to its $T_g$, which caused thermal reversion of the isomerization and a disappearance of the irradiated spot. In contrast, the white light exposure of polymer B produced no observable spot and therefore, negligible trans-cis isomerization. Since trans-cis isomerization reduces the linearity of the molecule, alters the position of the molecular dipole moment vector and reduces the ordering of a poled polymer system, it must have a negative impact on the material electro-optic coefficient. Polymer B of this invention is thus superior to the prior art in that it demonstrated a decreased tendency to undergo this type of isomerization.

EXAMPLE 80 strate bearing a 0.66 micron layer of thermal oxide. Over this was spun coat a 0.62 micron layer of Accuglass 410 spin-on-glass which was thermally cured at 160° C. A 1.41 micron thick film of a copolymer consisting of 80 mole percent methyl methacrylate and 20 mole percent:

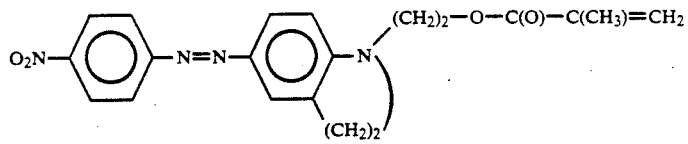

was spun over the Accuglass 410 layer from a 2-methoxyethyl ether solution followed by an oven bake to remove the solvent. The polymer layer was exposed for 3 hrs. to ultraviolet light from a 1000 W xenon lamp through a channel waveguide mask positioned so that the waveguide ran over the center of the long axis of the aluminum electrode. The width of the waveguide was 7 microns. Over this organic polymer film a second layer of Accuglass 410 was spin coated to a thickness of 0.60 micron. A second aluminum electrode was evaporated on top of the Accuglass 410 so that it was positioned directly above the first, with the waveguide area of the polymer sandwiched between them. Electrical connections were made to the upper and lower aluminum electrodes and the entire sample was placed in an oven and heated to 136° C. A dc voltage was applied between the two aluminum electrodes such that the polymer wave- Electro-Optic Performance of Selected Compounds of This Invention

| Active Monomer | $X^a$ | $E_{po}^b$ (MV/cm) | $\lambda^c$ (nm) | $r_{33}^d$ (pm/V) | $\lambda_{max}^e$ (nm) | Note |
|---|---|---|---|---|---|---|
| I. | 0.2 | 0.5 | 810 | 3.5 | 480 | Prior Art |
| II. | 0.2 | 0.5 | 810 | 4.7 | 530 | Added Conjugation |
| III. | 0.2 | 0.5 | 810 | 6.4 | 510 | Alkylene Bridge |
| IV. | 0.2 | 0.5 | 810 | 9.0 | 520 | Alkylene Bridge + Hydrogen Bond |

[a] Composition (mole fraction) copolymer with methyl methacrylate
[b] Poling field
[c] Wavelength of incident optical radiation
[d] Electro-optic coefficient - deduced from observed electro-optic response as in example 74
[e] Wavelength of peak absorption in lowest energy electronic absorption band

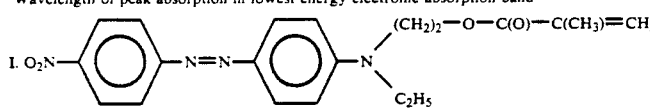

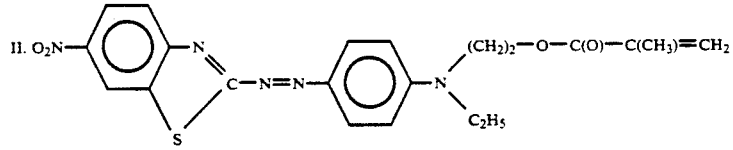

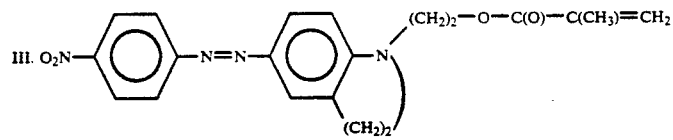

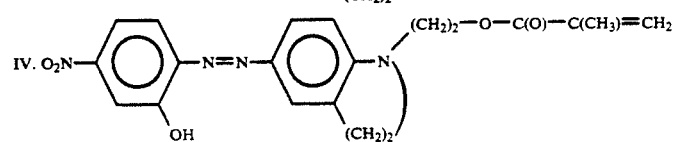

EXAMPLE 81

An aluminum electrode measuring 1 mm by 1 cm by 100 angstroms thick was evaporated onto a silicon subguide region experienced a static field of 0.72 MV/cm which was maintained until the sample was cooled to room temperature. The sample substrate was cleaved. Laser radiation at 810 nm was coupled into a single mode polarization preserving fiber optic cable. The opposite end of this fiber was brought into contact with the cleaved edge of the organic polymer film. When the fiber end was placed directly in front of the waveguide channel, laser light was coupled into the waveguide between the two electrodes. The output light from the other end of the waveguide was collected with a GRIN rod lens, passed through a Glan-Taylor polarizer and into a light detector. When a low voltage square wave signal was applied to the aluminum electrodes the amount of light detected was seen to rise and fall in concert with the applied voltage signal. This device constituted an example of an electro-optic phase modulator in channel waveguide form. The necessary voltage to induce a pi phase shift over the 1 cm path length of the electrodes was less than 5 V. The modulator was operated at frequencies up to 1 MHz. This example demonstrates that the method of the invention allows for the creation of channel waveguide structures in electro-optically active organic material.

EXAMPLE 82

In the manner of Example 81, channel waveguides are prepared in a copolymer of 80 mole percent methyl methacrylate and 20 mole percent:

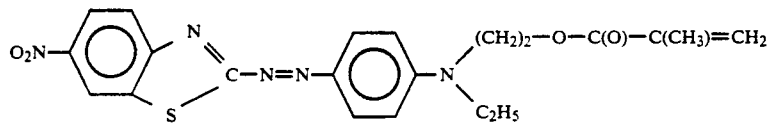

except that the waveguide regions are 3 to 10 microns in width. They are fiber coupled in the manner of Example 80 to demonstrate channel waveguiding. Application of a square wave potential results in modulation of the transmitted radiation.

EXAMPLE 83

Polymer compositions of this invention containing planarized molecular transducers with the compositions

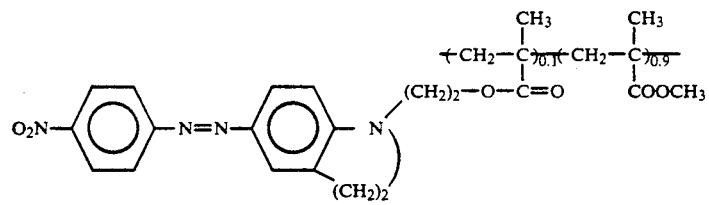

and

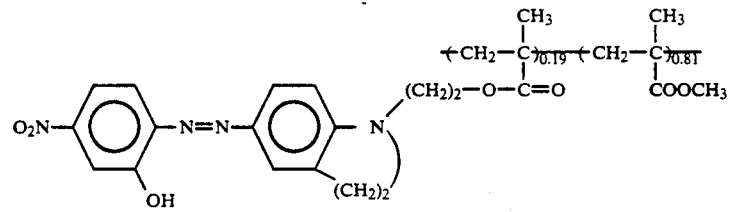

were prepared as described in Examples 33 and 61. Thin films of these polymers were spin coated upon transparent substrates of Corning 7059 glass with a 300 Angstrom thick layer of electrically conductive indium tin oxide (ITO) from filtered solutions of the polymers in 2-methoxy ethyl ether. The residual solvent was removed by baking the substrates in a convection oven. The dried films of the polymers from Example 33 and 61 had thicknesses of 2.6 micron and 1.1 micron respectively. Each film was overcoated with 0.75 micron of Allied Accuglass 410 spin-on-glass and baked again to dryness. A one cm by one cm gold electrode was sputtered on top of the spin-on-glass of each sample. The samples were separately heated to their glass transition temperatures (134° C. and 118° C., respectively) and a dc electric voltage was applied to the ITO and gold electrodes such that each polymer layer experienced a static field strength of 0.75 MV/cm. This electric field was maintained while the samples were cooled to room temperature and was then removed. The spin-on-glass and gold electrodes were then removed by rinsing the samples in methyl alcohol. These samples were rendered non-centrosymmetric by the above poling steps and as such were capable of acting as a nonlinear optical device for frequency conversion. This was verified by placing each in the beam of a 1.6 μm pulsed laser so that the laser beam passed through the poled region. When the samples were tilted so that the non-centrosymmetric axis of the films were at an angle to the 1.6 μm laser beam they produced light at 0.81 μm (two times the frequency). Both samples exhibited a maximum amount of 0.81 μm frequency doubled output at a sample angle of about 60° to the incoming laser beam. This type of frequency doubling verified the non-centrosymmetric nature of the poled polymer films of the invention. It also illustrates the utility of this material for optical frequency doubling devices.

Since various changes may be made in the invention, without departing from its spirit and essential characteristics, it is intended that all matter contained in the description shall be interpreted as illustrative only and not in a limiting sense, the scope of the invention being defined by the appended claims.

We claim:
1. A compound of the formula:

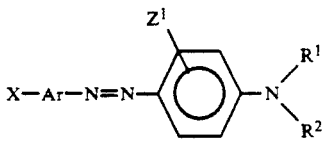

wherein:
(a) X is selected from the group consisting of:
   (1) —NO$_2$,
   (2) —CN,
   (3) —COOR$^3$ wherein R$^3$ is alkyl, straight chain, cyclic or branched having 1-20 carbon atoms,
   (4) —CH=C(CN)$_2$ and
   (5) —C(CN)=C(CN)$_2$;
(b) Ar is selected from the group consisting of

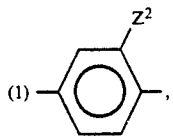

wherein Z$^2$ is
   (i) —H
   (ii) —OH
   (iii) —OC—(O)—CH=CH$_2$
   (iv) —OC—(O)—C(CH$_3$)=CH$_2$

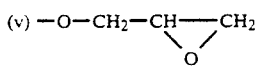

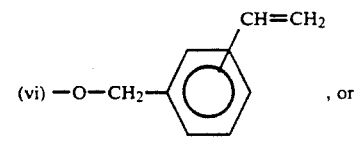

(vii) —O(CH$_2$)$_2$—OCH=CH$_2$;

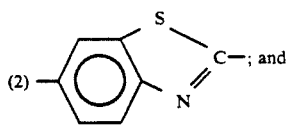

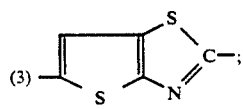

(c) Z$^1$ is selected from the group consisting of —H and —OH;
(d) R$^1$ is selected from the group consisting of
   (1) —H,
   (2) alkyl, straight chain, branched or cyclic, having about 1-20 carbon atoms,
   (3) —C$_n$H$_{2n}$OH, wherein n is an integer of from about 1-20,
   (4) —(CH$_2$)$_m$—CH=CH$_2$, wherein m is an integer of from about 1-20,

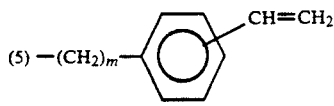

wherein m is an integer of from about 1-20 and the —CH=CH$_2$ substituent is in the m- or p- position,
   (6) —(CH$_2$)$_m$—O—M wherein m is an integer of from about 1-10, and wherein M is
      (i) —CH=CH$_2$,
      (ii) —C(O)—CH=CH$_2$,
      (iii) —C(O)—C(CH$_3$)=CH$_2$,

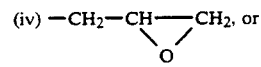

wherein the —CH=CH$_2$ substituent is in the m- or p-position and
   (7) an alkylene bridging group having 2 to 4 carbon atoms connecting the N atom to the o- position of the aromatic ring to which the N atom is attached; and
(e) R$_2$ is selected from the group consisting of
   (1) —H,
   (2) alkyl, straight chain, branched or cyclic, having about 1-20 carbon atoms,
   (3) —C$_n$H$_{2n}$OH wherein n is an integer of from about 1-20, and
   (4) an alkylene bridging group having 2 to 4 carbon atoms connecting the N atom to the o- position of the aromatic ring to which the N atom is attached;
with the proviso that at least one of R$^1$ and R$^2$ is an alkylene bridging group having from 2 to 4 carbon atoms connecting the N atom to o- position of the aromatic ring to which the N atom is attached.

2. A compound of the formula:

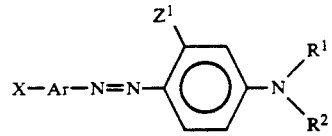

wherein:
(a) X is selected from the group consisting of:
   (1) —NO$_2$,
   (2) —CN,
   (3) —COOR$^3$ wherein R$^3$ is alkyl, straight chain, cyclic or branched having 1-20 carbon atoms,
   (4) —CH=C(CN)$_2$ and
   (5) —C(CN)=C(CN)$_2$;
(b) Ar is selected from the group consisting of

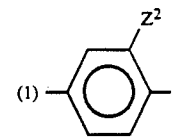

wherein $Z^2$ is
(i) —H
(ii) —OH
(iii) —OC—(O)—CH=CH$_2$
(iv) —OC—(O)—C(CH$_3$)=CH$_2$

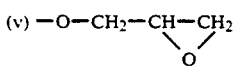

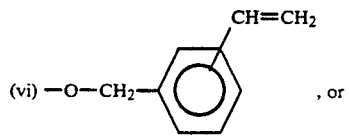

(vii) —O(CH$_2$)$_2$—OCH=CH$_2$;

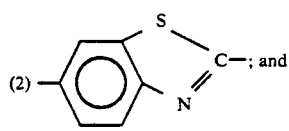

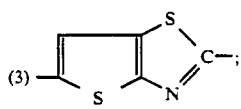

(c) $Z^1$ is selected from the group consisting of —H and —OH;
(d) $R^1$ is selected from the group consisting of
(1) —(CH$_2$)$_m$—CH=CH$_2$, wherein m is an integer of from

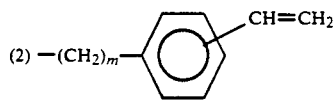

wherein m is an integer of from about 1-20 and the —CH=CH$_2$ substituent is in the m- or p- position,
(3) —(CH$_2$)$_m$—O—M wherein m is an integer of from about 1-10, and wherein M is
(i) —CH=CH$_2$,
(ii) —C(O)—CH=CH$_2$,
(iii) —C(O)—C(CH$_3$)=CH$_2$,

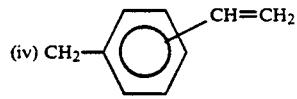

wherein the —CH=CH$_2$ substituent is in the m- or p-position and
(e) $R^2$ is selected from the group consisting of
(1) —H,
(2) alkyl, straight chain, branched or cyclic, having about 1-20 carbon atoms,
(3) —C$_n$H$_{2n}$OH, wherein n is an integer of from about 1-20, and
(4) an alkylene bridging group having 2 to 4 carbon atoms connecting the N atom to the o- position of the aromatic ring to which the N atom is attached;
with the proviso that $Z^1$ and $Z^2$ may not both be H unless either one or both of $R^1$ and $R^2$ represent an alkylene bridging group having 2 to 4 carbon atoms connecting the N atom to o- position of the aromatic ring to which the N atom is attached.

3. A compound of formula:

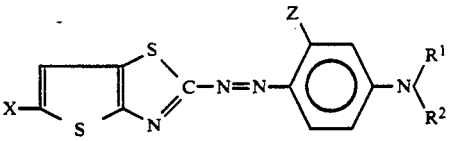

wherein:
(a) X is selected from the group consisting of:
(1) —NO$_2$,
(2) —CN,
(3) —COOR$^3$ wherein R$^3$ is alkyl, straight chain, cyclic or branched having 1-20 carbon atoms,
(4) —CH=C(CN)$_2$ and
(5) —C(CN)=C(CN)$_2$;
(b) Z is H or OH:
(c) $R^1$ is selected from the group consisting of
(1) —H,
(2) alkyl, straight chain, branched or cyclic, having about 1-20 carbon atoms,
(3) —C$_n$H$_{2n}$OH, wherein n is an integer of from about 1-20, and
(4) —(CH$_2$)$_m$—CH=CH$_2$, wherein m is an integer of from about 1-20,

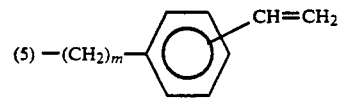

wherein m is an integer of from about 1-20 and the —CH=CH$_2$ substituent is in the m- or p- position,
(6) —(CH$_2$)$_m$—O—M wherein m is an integer of from about 1-10, and wherein M is
(i) —CH=CH$_2$,
(ii) —C(O)—CH=CH$_2$,
(iii) —C(O)—C(CH$_3$)=CH$_2$,

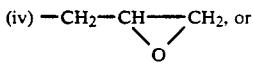

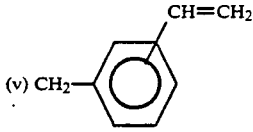

wherein the —CH=CH$_2$ substituent is in the m- or p-position and
(7) an alkylene bridging group having 2 to 4 carbon atoms connecting the N atom to the o- position of the aromatic ring to which the N atom is attached; and
(d) $R_2$ is selected from the group consisting of
(1) —H,
(2) alkyl, straight chain, branched or cyclic, having about 1-20 carbon atoms,
(3) —C$_n$H$_{2n}$OH wherein n is an integer of from about 1-20, and
(4) an alkylene bridging group having 2 to 4 carbon atoms connecting the N atom to the o- position of the aromatic ring to which the N atom is attached, wherein at least one of $R^1$ and $R^2$ is an alkylene bridging group having from 2 to 4 carbon atoms connecting the N atom to o- position of the aromatic ring to which the N atom is attached.

4. A compound according to claim 3 wherein X is $NO_2$.

5. A compound according to claim 3 wherein $R^1$ has a terminal $-CH=CH_2$ or $-C(CH_3)=CH_2$ group.

* * * * *